United States Patent
Bae et al.

(10) Patent No.: US 10,693,073 B2
(45) Date of Patent: Jun. 23, 2020

(54) FULLERENE DERIVATIVES AND ORGANIC ELECTRONIC DEVICE COMPRISING FULLERENE DERIVATIVES

(71) Applicant: LG CHEM, LTD., Seoul (KR)

(72) Inventors: Jaesoon Bae, Daejeon (KR); Jaechol Lee, Daejeon (KR); Jiyoung Lee, Daejeon (KR); Doowhan Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 384 days.

(21) Appl. No.: 15/110,308

(22) PCT Filed: Jan. 8, 2015

(86) PCT No.: PCT/KR2015/000202
§ 371 (c)(1),
(2) Date: Jul. 7, 2016

(87) PCT Pub. No.: WO2015/105354
PCT Pub. Date: Jul. 16, 2015

(65) Prior Publication Data
US 2016/0329498 A1    Nov. 10, 2016

(30) Foreign Application Priority Data

Jan. 8, 2014  (KR) .......... 10-2014-0002248
Aug. 14, 2014 (KR) .......... 10-2014-0106083

(51) Int. Cl.
*H01L 51/00* (2006.01)
*C07C 69/157* (2006.01)
(Continued)

(52) U.S. Cl.
CPC ........ *H01L 51/0047* (2013.01); *C01B 32/152* (2017.08); *C07C 33/38* (2013.01);
(Continued)

(58) Field of Classification Search
CPC .................. H01L 51/0046; H01L 51/0047
See application file for complete search history.

(56) References Cited

U.S. PATENT DOCUMENTS 6,448,412 B1 * 9/2002 Murphy ................ B82Y 10/00
                                              506/15
8,273,599 B2    9/2012 Bazan et al.
(Continued)

FOREIGN PATENT DOCUMENTS

CA    2117861 A1    4/1995
EP    2392555 A2   12/2011
(Continued)

OTHER PUBLICATIONS

Ohno et al. An Efficient Functionalization of [60 Fullerene. Diels-Alder Reaction using 1,3 Butadienes Substituted with Electron-Withdrawing and Electron-Donating (Silyoxy) Groups, 1996, Tetrahedron, vol. 52, No. 14, pp. 4983-4993. (Year: 1996).*
(Continued)

*Primary Examiner* — Daniel P Malley, Jr.
(74) *Attorney, Agent, or Firm* — Myers Bigel, P.A.

(57) ABSTRACT

The present specification relates to an organic electronic device including a fullerene derivative.

18 Claims, 1 Drawing Sheet

(51) Int. Cl.

| | |
|---|---|
| *C07C 69/612* | (2006.01) |
| *C07C 69/618* | (2006.01) |
| *C07C 69/738* | (2006.01) |
| *C07C 69/42* | (2006.01) |
| *C07C 211/00* | (2006.01) |
| *C07C 69/757* | (2006.01) |
| *C07C 229/42* | (2006.01) |
| *C07C 69/708* | (2006.01) |
| *C07C 69/54* | (2006.01) |
| *C09K 11/65* | (2006.01) |
| *C07C 69/78* | (2006.01) |
| *C07C 33/38* | (2006.01) |
| *C07C 69/716* | (2006.01) |
| *C07C 69/24* | (2006.01) |
| *C07C 69/76* | (2006.01) |
| *C01B 32/152* | (2017.01) |
| *C07C 43/168* | (2006.01) |
| *C07C 53/08* | (2006.01) |
| *C07C 59/84* | (2006.01) |
| *C07C 63/06* | (2006.01) |
| *C07C 63/36* | (2006.01) |
| *C07C 63/44* | (2006.01) |
| *C07D 333/38* | (2006.01) |
| *H01L 51/42* | (2006.01) |
| *B82Y 30/00* | (2011.01) |
| *B82Y 40/00* | (2011.01) |

(52) U.S. Cl.
CPC ............ *C07C 43/168* (2013.01); *C07C 53/08* (2013.01); *C07C 59/84* (2013.01); *C07C 63/06* (2013.01); *C07C 63/36* (2013.01); *C07C 63/44* (2013.01); *C07C 69/157* (2013.01); *C07C 69/24* (2013.01); *C07C 69/42* (2013.01); *C07C 69/54* (2013.01); *C07C 69/612* (2013.01); *C07C 69/618* (2013.01); *C07C 69/708* (2013.01); *C07C 69/716* (2013.01); *C07C 69/738* (2013.01); *C07C 69/757* (2013.01); *C07C 69/76* (2013.01); *C07C 69/78* (2013.01); *C07C 211/00* (2013.01); *C07C 229/42* (2013.01); *C07D 333/38* (2013.01); *C09K 11/65* (2013.01); *B82Y 30/00* (2013.01); *B82Y 40/00* (2013.01); *C07C 2601/04* (2017.05); *C07C 2601/08* (2017.05); *C07C 2602/10* (2017.05); *C07C 2603/24* (2017.05); *C07C 2603/50* (2017.05); *C07C 2604/00* (2017.05); *H01L 51/0036* (2013.01); *H01L 51/0037* (2013.01); *H01L 51/0043* (2013.01); *H01L 51/424* (2013.01); *H01L 51/4253* (2013.01); *Y02E 10/549* (2013.01); *Y10S 977/738* (2013.01); *Y10S 977/847* (2013.01); *Y10S 977/932* (2013.01)

(56) References Cited

U.S. PATENT DOCUMENTS

| | | | |
|---|---|---|---|
| 2003/0113940 A1* | 6/2003 | Erlanger | A61K 51/0495 436/524 |
| 2009/0176995 A1 | 7/2009 | Toru et al. | |
| 2012/0004476 A1 | 1/2012 | Yoon et al. | |
| 2013/0306944 A1 | 11/2013 | Kronholm et al. | |

FOREIGN PATENT DOCUMENTS

| | | | |
|---|---|---|---|
| EP | 2445026 A1 | | 4/2012 |
| JP | 07-187627 A | | 7/1995 |
| JP | 2009-135237 A | | 6/2009 |
| JP | 2011-124361 A | | 6/2011 |
| JP | 2012-079832 A | | 4/2012 |
| JP | 2012-089538 A | | 5/2012 |
| JP | 2014181238 A | * | 9/2014 |
| KR | 10-2010-0062579 A | | 6/2010 |
| KR | 10-1059783 B1 | | 8/2011 |
| KR | 10-2013-0027284 A | | 3/2013 |

OTHER PUBLICATIONS

ChEBI "ethoxycarbonyl group", website—https://www.ebi.ac.uk/chebi/searchId.do?chebild=CHEBI%3A52109, All Pages. (Year: 2018).*
PubChem "ethyl methyl ether", website https://pubchem.ncbi.nlm.nih.gov/compound/Methoxyethane#section=Top, All Pages. (Year: 2018).*
He et al., "Novel fullerene acceptors: synthesis and application in low band gap polymer solar cells", Journal of Materials Chemistry, 2012 vol. 22, pp. 13391-13394. (Year: 2012).*
Waldauf et al., "Efficient charge carrier transfer from m-LPPP to C60 derivatives", Optical Materials, vol. 9, 1998, pp. 449-453. (Year: 1998).*
English machine translation of Wang "JP 2014-181238 A" provided by the EPO. (Year: 2018).*
Viana et al., "A novel fullerene lipoic acid derivative: Synthesis and preparation of self-assembled monolayers on gold", Surface Science, 601, All Pages. (Year: 2007).*
Tang: "Two-layer organic photovoltaic cell", Applied Physics Letters, vol. 48, No. 2, Jan. 13, 1986, pp. 183-185.
Yu, et al.: "Polymer Photovoltaic Cells: Enhanced Efficiencies via a Network of Internal Donor-Acceptor Heterojunctions", Science, vol. 270, Dec. 15, 1995, pp. 1789-1791.
Zhuang, et al.: "Fullerene derivatives as electron donor for organic photovoltaic cells", Applied Physics Letters, vol. 103, 2013, pp. 203301-1-203301-4.
An, et al.: "Unusual Regioselectivity in the Singlet Oxygen Ene Reaction of Cyclohexenobuckminsterfullerenes", XP000542840, American Chemical Society, The Journal of Organic Chemistry, vol. 60, No. 26, Dec. 29, 1995.
Janot, et al.: "[60]Fullerene and three [60]fullerene derivatives in membrane model environments", XP055363916, The Royal Society of Chemistry, The Journal of the Chemical Society, vol. 2, No. 2, Jan. 1, 2000, pp. 301-306.
Viana, A. S., et al., "A novel fullerene lipoic acid derivative: Synthesis and preparation of self-assembled monolayers on gold," Surface Science, 2007, 601(21), pp. 5062-5068.
Wan, Terence S. M., et al., "Separation of Fullerenes with Non-aqueous Capillary Electrophoresis," Separation of Fullerenes by Liquid Chromatography, Editor(s): Jinno, Kiyokatsu, Royal Society of Chemistry, Cambridge, 1999, pp. 161-176.

* cited by examiner

FULLERENE DERIVATIVES AND ORGANIC ELECTRONIC DEVICE COMPRISING FULLERENE DERIVATIVES

This application is a National Stage Entry of International Application No. PCT/KR2015/000202, filed Jan. 8, 2015, and claims the benefit of and priority to Korean Application No. 10-2014-0002248, filed Jan. 8, 2014, and Korean Application No. 10-2014-0106083, filed Aug. 14, 2014, all of which are incorporated herein by reference in their entirety for all purposes as if fully set forth herein.

TECHNICAL FIELD

This specification claims priority to and the benefits of Korean Patent Application No. 10-2014-0002248, filed with the Korean Intellectual Property Office on Jan. 8, 2014, and Korean Patent Application No. 10-2014-0106083, filed with the Korean Intellectual Property Office on Aug. 14, 2014, the entire contents of which are incorporated herein by reference.

The present specification relates to a fullerene derivative and an organic electronic device including the same.

BACKGROUND ART

An organic electronic device means a device that needs charge exchanges between an electrode and an organic material using holes and/or electrons. An organic electronic device can be categorized into two main groups depending on operation principles. First is an electric device in which excitons form in an organic material layer by the photons brought into the device from an external light source, these excitons are separated into electrons and holes, and these electrons and holes are used as a current source (voltage source) by each of these being transferred to different electrodes. Second is an electronic device in which holes and/or electrons are injected to an organic material semiconductor that forms an interface with an electrode by applying voltage or current to two or more electrodes, and the device is operated by the injected electrons and holes.

Examples of an organic electronic device include an organic light emitting device, an organic solar cell, an organic transistor, and the like, and these all need a hole injection or transfer material, an electron injection or transfer material, or a light emitting material for the driving of the device. Hereinafter, an organic solar cell will be described in detail mostly, however, in the organic electronic devices described above, the hole injection or transfer material, the electron injection or transfer material, or the light emitting material is used under similar principles.

The possibility of an organic solar cell was first presented in 1970s, but the organic solar cell had no practical use since the efficiency was too low.

However, since C. W. Tang of Eastman Kodak showed the possibility of commercialization as various solar cells with a double layer structure using copper phthalocyanine (CuPc) and perylene tetracarboxylic acid derivatives in 1986, interests in organic solar cells and related researches have rapidly increased bringing in a lot of progresses.

Since then, organic solar cells have made innovative progresses in terms of efficiency as the concept of a bulk heterojunction (BHJ) was introduced by Yu et al. in 1995, and fullerene derivatives of which solubility is improved such as PCBM have been developed as an n-type semiconductor material.

However, problems such that fullerene, a starting material, is expensive, difficult to synthesize and does not have favorable solubility, are still blocking the development of electron acceptor materials. The development of electron donor materials having a low band gap and new electron acceptor materials having favorable charge mobility has been continuously attempted in order to replace existing materials.

PRIOR ART DOCUMENTS

Non-Patent Documents

Two-layer organic photovoltaic cell (C. W. Tang, Appl. Phys. Lett., 48, 183 (1996));
Efficiencies via Network of Internal Donor-Acceptor Heterojunctions (G. Yu, J. Gao, J. C. Hummelen, F. Wudl, A. J. Heeger, Science, 270, 1789 (1995))

DISCLOSURE

Technical Problem

An object of the present specification is to provide an organic electronic device including a fullerene derivative.

Technical Solution

One embodiment of the present specification provides a fullerene derivative represented by the following Chemical Formula 1.

[Chemical Formula 1]

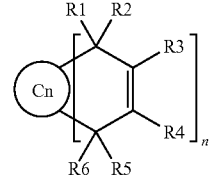

In Chemical Formula 1,
n is an integer of 1 to 5,
when n is 2 or greater, structures within a parenthesis are the same as or different from each other,
Cn is fullerene of $C_{60}$ to $C_{120}$,
R1 to R6 are the same as or different from each other, and each independently hydrogen; a halogen group; a nitro group; a cyano group; a carboxylic acid group; a hydroxyl group; a substituted or unsubstituted carbonyl group; a sulfo group ($-SO_3H$); a substituted or unsubstituted alkyl group; a substituted or unsubstituted alkoxy group; a substituted or unsubstituted cycloalkyl group; a substituted or unsubstituted alkenyl group; a substituted or unsubstituted ester group; a substituted or unsubstituted thioester group; a substituted or unsubstituted amide group; a substituted or unsubstituted ether group; a substituted or unsubstituted sulfonyl group ($-SO_2-$); a substituted or unsubstituted alkylthioxy group; a substituted or unsubstituted arylthioxy group; a substituted or unsubstituted alkylamine group; a substituted or unsubstituted arylamine group; a substituted or unsubstituted arylalkyl group; a substituted or unsubstituted heteroarylalkyl group; a substituted or unsubstituted aryl group; or a substituted or unsubstituted heteroring group, or adjacent substituents bond to each other to form a substituted or unsubstituted hydrocarbon ring; or a substituted or unsubstituted heteroring, at least one of R1 to R6 is

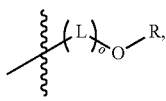

o is an integer of 1 to 3, and when o is an integer of 2 or greater, two or more Ls are the same as or different from each other, L is substituted or unsubstituted alkylene, and R is hydrogen; a carboxylic acid group; a substituted or unsubstituted carbonyl group; a substituted or unsubstituted alkyl group; a substituted or unsubstituted cycloalkyl group; a substituted or unsubstituted alkenyl group; a substituted or unsubstituted ester group; a substituted or unsubstituted thioester group; a substituted or unsubstituted amide group; a substituted or unsubstituted sulfonyl group ($-SO_2-$); a substituted or unsubstituted arylalkyl group; a substituted or unsubstituted aryl group; or a substituted or unsubstituted heteroring group.

One embodiment of the present specification provides an organic electronic device including a first electrode; a second electrode provided opposite to the first electrode; and one or more organic material layers provided between the first electrode and the second electrode, wherein one or more layers of the organic material layers include the fullerene derivative.

Advantageous Effects

An organic electronic device including a fullerene derivative according to one embodiment of the present specification exhibits an efficiency increase and/or a stability increase.

The fullerene derivative according to one embodiment of the present specification can be used in a pure form or as a mixture with impurities in an organic electronic device including an organic solar cell, and may be applied using a vacuum deposition method, a solution coating method and the like.

The organic electronic device including the fullerene derivative according to one embodiment of the present specification has excellent light efficiency and excellent thermal stability, and has improved lifespan properties.

REFERENCE NUMERAL

Figure 1:
FIG. 1 is a diagram showing an organic solar cell according to one embodiment of the present specification.
Figure 2:
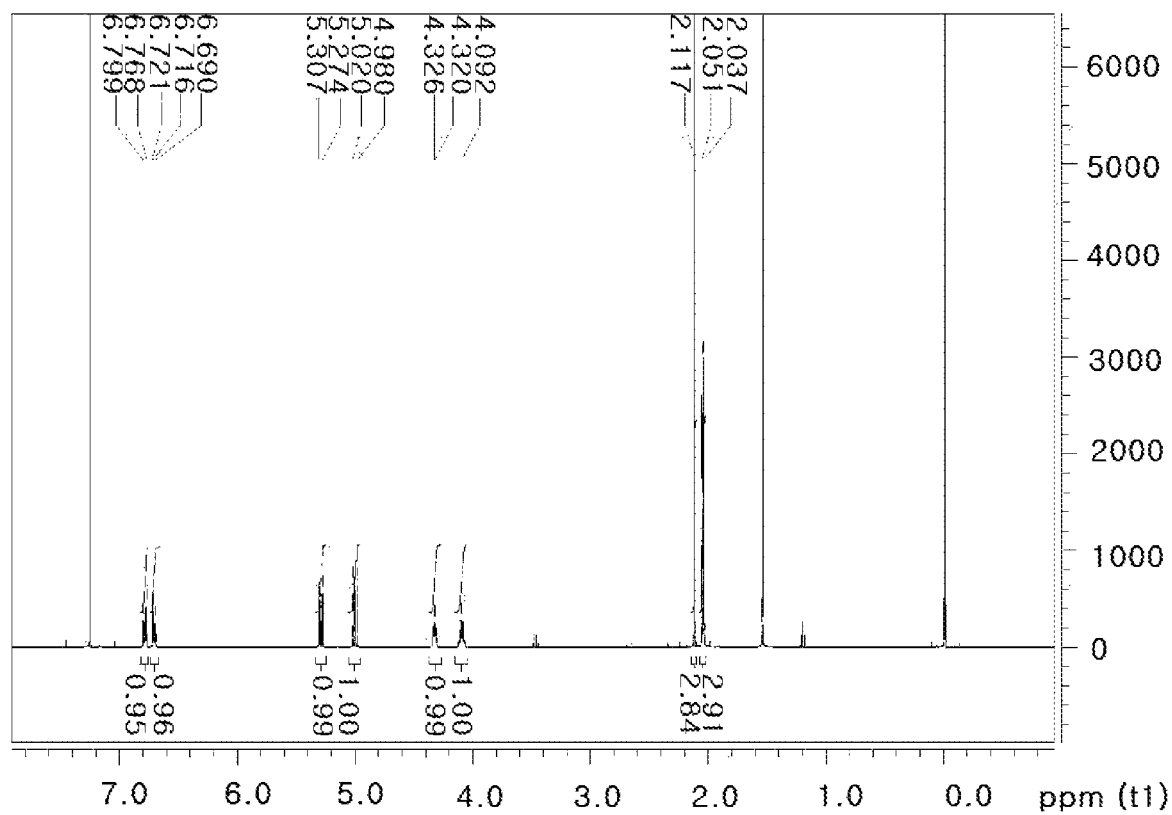
FIG. 2 is a diagram showing an NMR graph of Chemical Formula 1-1.

101: Substrate
102: First Electrode
103: Hole Transfer Layer
104: Photoactive Layer
105: Second Electrode

MODE FOR DISCLOSURE

Hereinafter, the present specification will be described in detail.

One embodiment of the present specification provides a fullerene derivative represented by Chemical Formula 1.

The fullerene derivative according to one embodiment of the present specification includes at least one of

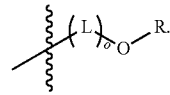

In this case, morphology properties with an electron donor may be changed depending on the types of L and the types of R, and accordingly, efficiency may increase.

The fullerene derivative according to one embodiment of the present specification may have excellent improved solubility in an organic solvent by controlling L and R.

For example, when L is an alkylene group, a new crystalline film structure may be formed with a hydrophobic property together with an alkyl group introduced in order to improve the solubility of an electron donor.

In one embodiment of the present specification, the fullerene derivative represented by Chemical Formula 1 is represented by the following Chemical Formula 2 or 3.

[Chemical Formula 2]

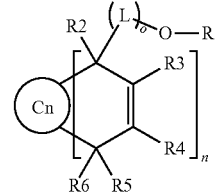

[Chemical Formula 3]

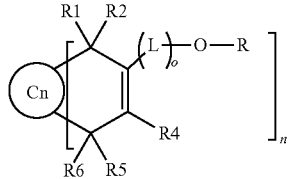

In Chemical Formulae 2 and 3,

The definitions of R, Cn, n, o, L and R1 to R6 may be the same as the definitions made in Chemical Formula 1.

In one embodiment of the present specification, R is a substituted or unsubstituted carbonyl group.

One embodiment of the present specification provides an organic electronic device in which the fullerene derivative represented by Chemical Formula 1 is a fullerene derivative represented by the following Chemical Formula 2-1 or Chemical Formula 3-1.

[Chemical Formula 2-1]

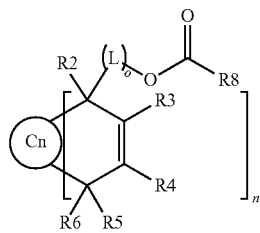

-continued

[Chemical Formula 3-1]

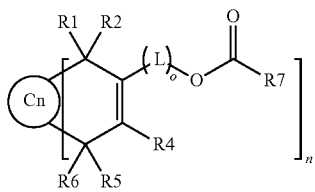

In Chemical Formulae 2-1 and 3-1,

The definitions of Cn, n, o, L and R1 to R6 are the same as the definitions made in Chemical Formula 1, and R7 and R8 are the same as or different from each other, and each independently hydrogen; a substituted or unsubstituted alkyl group; a substituted or unsubstituted cycloalkyl group; a substituted or unsubstituted alkenyl group; a substituted or unsubstituted ether group; a substituted or unsubstituted sulfonyl group; a substituted or unsubstituted arylalkyl group; substituted or unsubstituted cyclic ketone; a substituted or unsubstituted aryl group; or a substituted or unsubstituted heteroring group.

Examples of the substituents are described below, however, the substituents are not limited thereto.

The term "a substituted or unsubstituted" in the present specification means being substituted with one or more substituents selected from the group consisting of a halogen group; a nitro group; a cyano group; a carboxyl group; a hydroxyl group; a carbonyl group; a sulfo group; an alkyl group; an allyl group; an alkoxy group; a cycloalkyl group; an alkenyl group; an ester group; an ether group; a sulfonyl group; a sulfoxy group; an arylalkyl group; an aryl group; and a heteroring group, or having no substituents, or being substituted with a substituent linking two or more substituents of the substituents illustrated above, or having no substituents. For example, "a substituent linking two or more substituents" may include a biphenyl group. In other words, a biphenyl group may be interpreted as an aryl group, or as a substituent linking 2 phenyl groups.

The term "substitution" means a hydrogen atom bonding to a carbon atom of a compound is changed to another substituent, and the position of substitution is not limited as long as it is a position at which a hydrogen atom is substituted, that is, a position at which a substituent can substitute, and when two or more substituents substitute, the two or more substituents may be the same as or different from each other.

In the present specification, the halogen group may include fluorine, chlorine, bromine or iodine.

In the present specification, the carbonyl group may be represented by

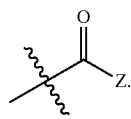

Herein, Z is hydrogen; a substituted or unsubstituted alkyl group having 1 to 20 carbon atoms; a substituted or unsubstituted cycloalkyl group having 3 to 60 carbon atoms; a substituted or unsubstituted arylalkyl group having 7 to 50 carbon atoms; a substituted or unsubstituted aryl group having 6 to 60 carbon atoms; a substituted or unsubstituted heteroring group having 2 to 60 carbon atoms.

In the present specification, the alkyl group may be linear or branched, and the number of carbon atoms, although not particularly limited, is preferably 1 to 40. Specific examples thereof include a methyl group, an ethyl group, a propyl group, a butyl group, a pentyl group, a hexyl group, a heptyl group, an octyl group, a nonanyl group, a decanyl group, an undecanyl group, a dodecanyl group, an icosanyl group and the like, but are not limited thereto, and these may be branched or substituted forms may also be used.

In the present specification, the cycloalkyl group is not particularly limited, but preferably has 3 to 60 carbon atoms, and specific examples thereof include cyclopropyl, cyclobutyl, cyclopentyl, cyclohexyl, cycloheptyl, cyclooctyl, a norbonyl group, an adamanty group and the like, but are not limited thereto, and substituted forms thereof may also be used.

In the present specification, the alkoxy group may be linear, branched or cyclic. The number of carbon atoms in the alkoxy group is not particularly limited, but is preferably 1 to 40. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, 2-ethylhexyloxy, 2-methylheptyloxy, 2-propylbutyloxy, n-nonyloxy, n-decyloxy and the like, but are not limited thereto.

In the present specification, the number of carbon atoms in the arylalkyl group is not particularly limited, however, in one embodiment of the present specification, the number of carbon atoms in the arylalkyl group is 7 to 50. Specifically, the aryl part has 6 to 49 carbon atoms, and the alkyl part has 1 to 44 carbon atoms. Specific examples thereof include a phenylmethyl group, a phenylethyl group, a phenylpropyl group, a phenylisopropyl group, a phenylbutyl group, a phenylisobutyl group, a phenylpentyl group, a phenylisopentyl group, a phenylhexyl group, a phenylisohexyl group, a phenylheptyl group, a phenyloctyl group, a phenylnonanyl group, a phenyldecanyl group, a naphthylmethyl group, a naphthylethyl group, a naphthylpropyl group, a naphthylisopropyl group, a pyrenylmethyl group, a pyrenylethyl group, a pyrenylpropyl group, a pyrenylisopropyl group, a pyrrolylmethyl group, a pyrrolylethyl group, an aminophenylmethyl group, a nitrophenylmethyl group, a cyanophenylmethyl group, a 1-hydroxy-2-phenylisopropyl group, a 1-chloro-2-phenylisopropyl group, a thiophenylmethyl group, a thiophenylethyl group, a thiophenylpropyl group, a thiophenylisopropyl group, a thiophenylbutyl group and the like, but are not limited thereto, and substituted forms thereof may also be used.

In the present specification, the alkenyl group may be linear or branched, and although not particularly limited, the number of carbon atoms is preferably 2 to 40. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the general formula of the thioester group may be represented by

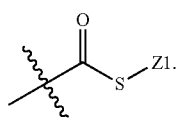

Herein, Z1 is hydrogen; a substituted or unsubstituted alkyl group having 1 to 60 carbon atoms; a substituted or unsubstituted cycloalkyl group having 3 to 60 carbon atoms; a substituted or unsubstituted arylalkyl group having 7 to 50 carbon atoms; a substituted or unsubstituted aryl group having 6 to 60 carbon atoms; or a substituted or unsubstituted heteroring group having 2 to 60 carbon atoms, and including one or more of N, O and S atoms.

The general formula of the amide group of the present specification may be represented by

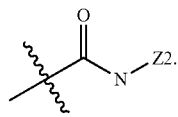

Herein, Z2 is hydrogen; a substituted or unsubstituted alkyl group having 1 to 60 carbon atoms; a substituted or unsubstituted cycloalkyl group having 3 to 60 carbon atoms; a substituted or unsubstituted arylalkyl group having 7 to 50 carbon atoms; a substituted or unsubstituted aryl group having 6 to 60 carbon atoms; or a substituted or unsubstituted heteroring group having 2 to 60 carbon atoms, and including one or more of N, O and S atoms.

In the present specification, the aryl group may be monocyclic, and although not particularly limited, the number of carbon atoms is preferably 6 to 60. Specific examples of the aryl group include a monocyclic aromatic such as a phenyl group, a biphenyl group and a terphenyl group, and a multicyclic aromatic such as a naphthyl group, an anthracenyl group, a phenanthrenyl group, a pyrenyl group, a perylenyl group, a tetracenyl group, a crycenyl group, a fluorenyl group, an acenaphthacenyl group, a triphenylene group and a fluoranthene group, and the like, but the examples are not limited thereto and these groups may be substituted with additional substituents.

In the present specification, the heteroring group is a group including one or more atoms that are not carbon, that is, heteroatoms, and specifically, the heteroatoms may include one or more atoms selected from the group consisting of O, N, S and the like. The number of carbon atoms in the heteroring group is not particularly limited, but is preferably 2 to 60. Examples of the heteroring group include a thiophene group, a furan group, a pyrrole group, an imidazole group, a triazole group, an oxazole group, an oxadiazole group, a triazole group, a pyridyl group, a bipyridyl group, a triazine group, an acridyl group, a pyridazine group, a quinolinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a dibenzofuranyl group and the like, but the examples are not limited thereto and these groups may be substituted with additional substituents.

In the present specification, the general formula of the ester group may be represented by

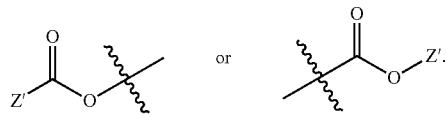

Herein, Z' is hydrogen; a substituted or unsubstituted alkyl group having 1 to 20 carbon atoms; a substituted or unsubstituted cycloalkyl group having 3 to 60 carbon atoms; a substituted or unsubstituted arylalkyl group having 7 to 50 carbon atoms; a heteroarylalkyl group having 2 to 60 carbon atoms; a substituted or unsubstituted carbonyl group having 1 to 40 carbon atoms; a substituted or unsubstituted aryl group having 6 to 60 carbon atoms; or a substituted or unsubstituted heteroring group having 2 to 60 carbon atoms, and including one or more of N, O and S atoms.

In the present specification,

means a site that bonds to other substituents or bonding sites.

Adjacent substituents in the present specification mean substituents that substitute neighboring carbons such as R1 or R2 and R3; R3 and R4; R4 and R5 or R6; and R1 or R2 and R5 or R6.

Adjacent groups bonding to each other to form a hydrocarbon ring or a heteroring in the present specification means adjacent substituents forming a bond to form a 5-membered to 7-membered monocyclic or multicyclic hydrocarbon ring, or a 5-membered to 7-membered monocyclic or multicyclic heteroring group.

The hydrocarbon ring in the present specification includes all of a cycloalkyl group; a cycloalkenyl group; an aromatic ring group; or an aliphatic ring group, may be monocyclic or multicyclic, and all includes a fused ring in which one, two or more of these bond.

The heteroring formed in the present specification means that at least one carbon atom in the hydrocarbon ring is substituted with an N, O, or S atom, and the formed heteroring may be an aliphatic ring or an aromatic ring, and may be monocyclic or multicyclic.

Specifically, a fused cyclopropane ring, a fused cyclopropene ring, a fused cyclobutane ring, a fused cyclobutene ring, a fused cyclopentane ring, a fused cyclopentene ring, a fused cyclopentadiene ring, a fused cyclohexane ring, a fused cyclohexene ring, a fused cyclohexadiene ring, a fused norbornane ring, a fused bicyclo[2,2,2]octene ring and the like are included in the present specification, but the examples are not limited thereto.

In one embodiment of the present specification, o is 1.

In another embodiment, L is a substituted or unsubstituted alkylene group.

In one embodiment, L is an alkylene group.

In another embodiment, L is a methylene group.

In one embodiment of the present specification, R1 is hydrogen.

In one embodiment of the present specification, R2 is hydrogen.

In one embodiment of the present specification, R3 is hydrogen.

In one embodiment of the present specification, R4 is hydrogen.

In one embodiment of the present specification, R5 is hydrogen.

In another embodiment, R5 is a substituted or unsubstituted alkyl group.

In one embodiment, R5 is a methyl group.

In one embodiment, R6 is hydrogen.

In one embodiment, R6 is a substituted or unsubstituted alkyl group.

In another embodiment, R6 is a methyl group.

In one embodiment of the present specification, R is hydrogen; a substituted or unsubstituted alkyl group; or a substituted or unsubstituted carbonyl group.

In one embodiment of the present specification, R is hydrogen.

In one embodiment of the present specification, R is a substituted or unsubstituted alkyl group.

In one embodiment of the present specification, R is a substituted or unsubstituted an octyl group.

In one embodiment of the present specification, R is an octyl group.

In one embodiment of the present specification, R is a substituted or unsubstituted carbonyl group.

In one embodiment of the present specification, R is a carbonyl group unsubstituted or substituted with a substituent selected from the group consisting of a substituted or unsubstituted alkyl group, a substituted or unsubstituted aryl group, substituted or unsubstituted cyclic ketone, and a substituted or unsubstituted heteroring group including one or more of N, O and S atoms.

In one embodiment of the present specification, R is a carbonyl group unsubstituted or substituted with a substituted or unsubstituted alkyl group.

In one embodiment, R is a carbonyl group unsubstituted or substituted with an alkyl group.

In one embodiment, R is a carbonyl group unsubstituted or substituted with a branched alkyl group.

In another embodiment, R is a carbonyl group substituted with a 2-methylpentyl group.

In one embodiment, R is a carbonyl group unsubstituted or substituted with a linear alkyl group.

In one embodiment, R is a carbonyl group substituted with a methyl group.

In one embodiment, R is a carbonyl group substituted with an octyl group.

In one embodiment, R is a carbonyl group substituted with a 1-octyl group.

In another embodiment, R is a carbonyl group substituted with a 3-octyl group.

In one embodiment, R is a carbonyl group substituted with an alkyl group unsubstituted or substituted with a substituted or unsubstituted aryl group.

In one embodiment, R is a carbonyl group substituted with an alkyl group unsubstituted or substituted with a phenyl group.

In another embodiment, R is a carbonyl group substituted with a propyl group unsubstituted or substituted with a phenyl group.

In another embodiment, R is a carbonyl group substituted with an alkyl group substituted with a phenyl group unsubstituted or substituted with an amine group.

In one embodiment of the present specification, R is a carbonyl group substituted with a pentyl group substituted with a phenyl group.

In another embodiment, R is a carbonyl group substituted with an ethyl group substituted with a phenyl group substituted with an amine group substituted with an alkyl group and/or an aryl group.

In one embodiment, R is a carbonyl group substituted with an ethyl group substituted with a phenyl group substituted with a hexylphenylamine group.

In another embodiment, R is a carbonyl group substituted with an alkyl group substituted with an aryl group unsubstituted or substituted with a substituted or unsubstituted heteroring group including one or more of N, O and S atoms.

In another embodiment, R is a carbonyl group substituted with an alkyl group substituted with a phenyl group substituted with a substituted or unsubstituted heteroring group including one or more N atoms.

In one embodiment of the present specification, R is a carbonyl group substituted with an ethyl group substituted with a phenyl group substituted with a carbazole group.

In another embodiment, R is a carbonyl group substituted with an ethyl group substituted with a phenyl group substituted with a benzimidazole group substituted with a phenyl group.

In one embodiment, R is a carbonyl group substituted with an alkyl group substituted with an alkoxy group.

In another embodiment, R is a carbonyl group substituted with tetraoxatridecanyl.

In another embodiment, R is a carbonyl group substituted with an alkyl group unsubstituted or substituted with a substituted or unsubstituted carbonyl group.

In one embodiment of the present specification, R is a carbonyl group substituted with an alkyl group substituted with a carbonyl group unsubstituted or substituted with an aryl group.

In one embodiment, R is a carbonyl group substituted with an alkyl group substituted with a carbonyl group substituted with a phenyl group.

In one embodiment of the present specification, R is a carbonyl group substituted with an ethyl group substituted with a carbonyl group substituted with a phenyl group.

In one embodiment of the present specification, R is a carbonyl group substituted with a butyl group substituted with a carbonyl group substituted with a phenyl group.

In one embodiment of the present specification, R is a carbonyl group substituted with an alkyl group substituted with a carbonyl group unsubstituted or substituted with an alkyl group.

In another embodiment, R is a carbonyl group substituted with a butyl group substituted with a carbonyl group substituted with an alkyl group.

In another embodiment of the present specification, R is a carbonyl group substituted with a butyl group substituted with a carbonyl group substituted with a methyl group.

In one embodiment of the present specification, R is a carbonyl group substituted with an alkyl group substituted with a substituted or unsubstituted ester group.

In one embodiment, R is a carbonyl group substituted with an alkyl group substituted with an ester group substituted with an alkyl group.

In another embodiment, R is a carbonyl group substituted with a propyl group substituted with an ester group substituted with a methyl group.

In one embodiment of the present specification, R is a carbonyl group substituted with an alkyl group substituted with a substituted or unsubstituted cyclic ketone group.

In one embodiment of the present specification, R is a carbonyl group substituted with an alkyl group substituted with a substituted or unsubstituted chromenone group.

In one embodiment of the present specification, R is a carbonyl group substituted with an alkyl group substituted with a chromenone group substituted with a halogen group.

In another embodiment, R is a carbonyl group substituted with an ethyl group substituted with a chromenone group substituted with fluorine.

In one embodiment of the present specification, R is a carbonyl group substituted with an alkyl group unsubstituted or substituted with a substituted or unsubstituted heteroring group including one or more of N, O and S atoms.

In one embodiment, R is a carbonyl group substituted with an alkyl group substituted with a substituted or unsubstituted heteroring group including one or more S atoms.

In one embodiment, R is a carbonyl group substituted with an alkyl group substituted with a thiophene group unsubstituted or substituted with an alkyl group.

In another embodiment, R is a carbonyl group substituted with a propyl group substituted with a thiophene group substituted with a hexyl group.

In another embodiment, R is a carbonyl group unsubstituted or substituted with a substituted or unsubstituted aryl group.

In one embodiment of the present specification, R is a carbonyl group substituted with a substituted or unsubstituted phenyl group.

In one embodiment of the present specification, R is a carbonyl group substituted with a phenyl group.

In another embodiment, R is a carbonyl group substituted with a substituted or unsubstituted naphthyl group.

In another embodiment, R is a carbonyl group substituted with a naphthyl group.

In one embodiment, R is a carbonyl group substituted with a substituted or unsubstituted anthracenyl group.

In one embodiment, R is a carbonyl group substituted with an anthracenyl group.

In another embodiment, R is a carbonyl group substituted with a substituted or unsubstituted pyrene group.

In another embodiment, R is a carbonyl group substituted with a pyrene group.

In one embodiment of the present specification, R is a carbonyl group unsubstituted or substituted with a substituted or unsubstituted heteroring group including one or more of N, O and S atoms.

In one embodiment, R is a carbonyl group unsubstituted or substituted with a substituted or unsubstituted heteroring group including one or more S atoms.

In one embodiment of the present specification, R is a carbonyl group unsubstituted or substituted with a substituted or unsubstituted thiophene group.

In one embodiment, R is a carbonyl group substituted with a thiophene group substituted with a heteroring group including one or more S atoms substituted with an alkyl group.

In one embodiment, R is a carbonyl group substituted with a thiophene group substituted with a thiophene group substituted with an alkyl group.

In one embodiment of the present specification, R is a carbonyl group substituted with a thiophene group substituted with a thiophene group unsubstituted or substituted with a hexyl group.

In one embodiment of the present specification, R is a carbonyl group substituted with a substituted or unsubstituted cyclic ketone group.

In one embodiment, R is a carbonyl group substituted with cyclic butanone.

In another embodiment, R is a carbonyl group substituted with cyclic pentanone.

In one embodiment, R is a carbonyl group substituted with naphthalenone.

In another embodiment, R is a carbonyl group substituted with dihydronaphthalenone.

In one embodiment, R is a carbonyl group substituted with a chromenone group.

In one embodiment of the present specification, R is a carbonyl group substituted with an alkenyl group.

In another embodiment, R is a carbonyl group substituted with a substituted or unsubstituted ethenyl group.

In one embodiment, R is a carbonyl group substituted with an ethenyl group.

In another embodiment, R is a carbonyl group substituted with an ethenyl group substituted with a phenyl group.

In another embodiment, R is a carbonyl group substituted with an ethenyl group substituted with an alkyl group.

In another embodiment, R is a carbonyl group substituted with an ethenyl group substituted with a methyl group.

In one embodiment of the present specification, R7 and R8 are the same as or different from each other, and each independently a substituted or unsubstituted alkyl group; a substituted or unsubstituted alkenyl group; a substituted or unsubstituted aryl group; substituted or unsubstituted cyclic ketone; or a substituted or unsubstituted heteroring group.

In one embodiment of the present specification, R8 is a substituted or unsubstituted alkyl group.

In one embodiment, R8 is a branched alkyl group.

In another embodiment, R8 is a 2-methylpentyl group.

In one embodiment, R8 is a linear alkyl group.

In one embodiment, R8 is a substituted or unsubstituted methyl group.

In another embodiment, R8 is a methyl group.

In one embodiment, R8 is an octyl group.

In one embodiment, R8 is a 1-octyl group.

In another embodiment, R8 is a 3-octyl group.

In one embodiment, R8 is an alkyl group unsubstituted or substituted with a substituted or unsubstituted aryl group.

In one embodiment, R8 is an alkyl group unsubstituted or substituted with a phenyl group.

In another embodiment, R8 is a propyl group unsubstituted or substituted with a phenyl group.

In one embodiment of the present specification, R8 is a pentyl group unsubstituted or substituted with a phenyl group.

In another embodiment, R8 is an alkyl group substituted with a phenyl group unsubstituted or substituted with an amine group.

In another embodiment, R8 is an ethyl group substituted with a phenyl group substituted with an amine group substituted with an alkyl group and/or an aryl group.

In one embodiment, R8 is an ethyl group substituted with a phenyl group substituted with a hexylphenylamine group.

In another embodiment, R8 is an alkyl group substituted with an aryl group unsubstituted or substituted with a substituted or unsubstituted heteroring group including one or more of N, O and S atoms.

In another embodiment, R8 is an alkyl group substituted with a phenyl group substituted with a substituted or unsubstituted heteroring group including one or more N atoms.

In one embodiment of the present specification, R8 is an ethyl group substituted with a phenyl group substituted with a carbazole group.

In another embodiment, R8 is an ethyl group substituted with a phenyl group substituted with a benzimidazole group substituted with a phenyl group.

In one embodiment, R8 is an alkyl group substituted with an alkoxy group.

In another embodiment, R8 is a tetraoxatridecanyl group.

In one embodiment of the present specification, R8 is an alkyl group unsubstituted or substituted with a substituted or unsubstituted carbonyl group.

In another embodiment, R8 is an alkyl group substituted with a carbonyl group unsubstituted or substituted with an aryl group.

In one embodiment, R8 is an alkyl group substituted with a carbonyl group substituted with a phenyl group.

In one embodiment of the present specification, R8 is an ethyl group substituted with a carbonyl group substituted with a phenyl group.

In one embodiment of the present specification, R8 is a butyl group substituted with a carbonyl group substituted with a phenyl group.

In one embodiment of the present specification, R8 is an alkyl group substituted with a carbonyl group unsubstituted or substituted with an alkyl group.

In another embodiment, R8 is a butyl group substituted with a carbonyl group substituted with an alkyl group.

In another embodiment of the present specification, R8 is a butyl group substituted with a carbonyl group substituted with a methyl group.

In one embodiment of the present specification, R8 is an alkyl group substituted with a substituted or unsubstituted ester group.

In one embodiment, R8 is an alkyl group substituted with an ester group substituted with an alkyl group.

In another embodiment, R8 is a propyl group substituted with an ester group substituted with a methyl group.

In one embodiment of the present specification, R8 is an alkyl group substituted with a substituted or unsubstituted cyclic ketone group.

In one embodiment of the present specification, R8 is an alkyl group substituted with a substituted or unsubstituted chromenone group.

In one embodiment of the present specification, R8 is an alkyl group substituted with a chromenone group substituted with a halogen group.

In another embodiment, R8 is an ethyl group substituted with a chromenone group substituted with fluorine.

In one embodiment of the present specification, R8 is an alkyl group unsubstituted or substituted with a substituted or unsubstituted heteroring group including one or more of N, O and S atoms.

In one embodiment, R8 is an alkyl group substituted with a substituted or unsubstituted heteroring group including one or more S atoms.

In one embodiment, R8 is an alkyl group substituted with an a thiophene group unsubstituted or substituted with an alkyl group.

In another embodiment, R8 is a propyl group substituted with a thiophene group substituted with a hexyl group.

In another embodiment, R8 is a substituted or unsubstituted aryl group.

In one embodiment, R8 is a substituted or unsubstituted phenyl group.

In another embodiment, R8 is a phenyl group.

In one embodiment of the present specification, R8 is a substituted or unsubstituted naphthyl group.

In another embodiment, R8 is a naphthyl group.

In another embodiment, R8 is a substituted or unsubstituted pyrene group.

In one embodiment, R8 is a pyrene group.

In another embodiment, R8 is a substituted or unsubstituted anthracene group.

In another embodiment, R8 is an anthracene group.

In one embodiment of the present specification, R8 is a substituted or unsubstituted heteroring group including one or more of N, O and S atoms.

In one embodiment of the present specification, R8 is a substituted or unsubstituted heteroring group including one or more S atoms.

In one embodiment of the present specification, R8 is a substituted or unsubstituted thiophene group.

In one embodiment, R8 is a thiophene group substituted with a thiophene group substituted with a heteroring group including one or more S atoms substituted with an alkyl group.

In one embodiment, R8 is a thiophene group substituted with a thiophene group substituted with an alkyl group.

In one embodiment of the present specification, R8 is a carbonyl group substituted with a thiophene group substituted with a thiophene group unsubstituted or substituted with a hexyl group.

In one embodiment of the present specification, R8 is a substituted or unsubstituted cyclic ketone group.

In one embodiment, R8 is a cyclic butanone group.

In another embodiment, R8 is a cyclic pentanone group.

In one embodiment, R8 is a naphthalenone group.

In another embodiment, R8 is a dihydronaphthalenone group.

In one embodiment, R8 is a chromenone group.

In one embodiment of the present specification, R8 is a substituted or unsubstituted alkenyl group.

In another embodiment, R8 is a substituted or unsubstituted ethenyl group.

In one embodiment, R8 is an ethenyl group.

In another embodiment, R8 is an ethenyl group substituted with a phenyl group.

In another embodiment, R8 is an ethenyl group substituted with an alkyl group.

In another embodiment, R8 is an ethenyl group substituted with a methyl group.

In one embodiment of the present specification, the fullerene derivative represented by Chemical Formula 1 is represented by any one of the following Chemical Formulae 1-1-1 to 1-1-31.

Chemical Formula 1-1-1

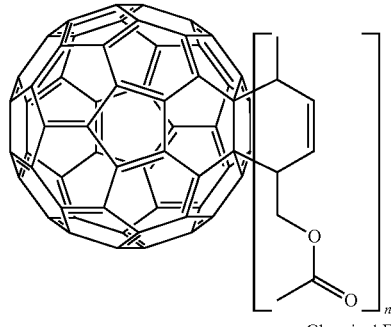

Chemical Formula 1-1-2

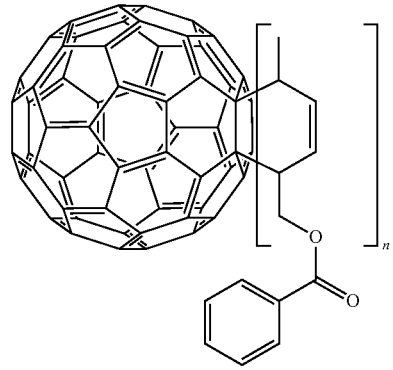

Chemical Formula 1-1-3
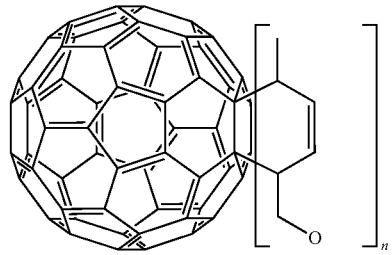
Chemical Formula 1-1-4
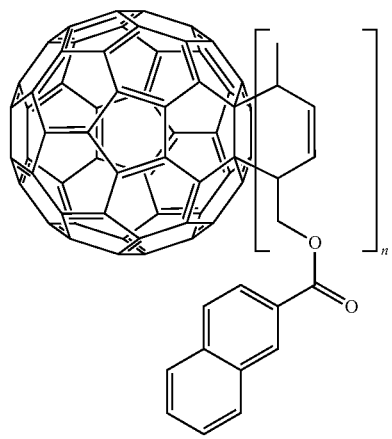
Chemical Formula 1-1-5
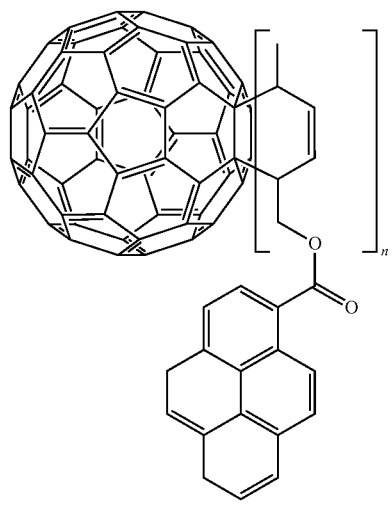
Chemical Formula 1-1-6
Chemical Formula 1-1-7
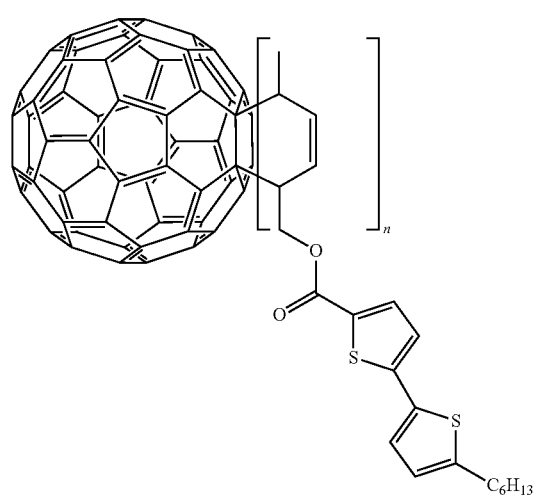
Chemical Formula 1-1-8
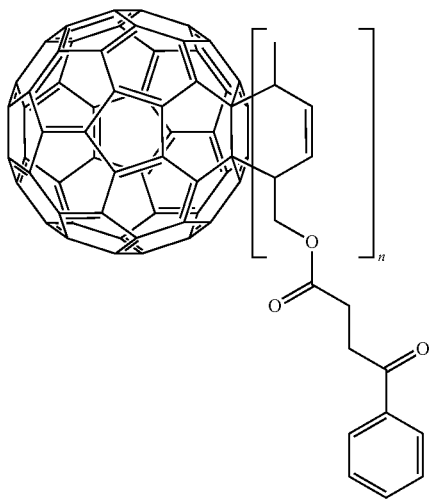

Chemical Formula 1-1-9
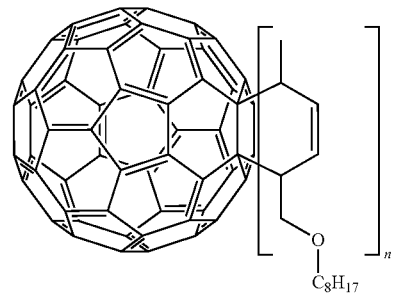
Chemical Formula 1-1-10
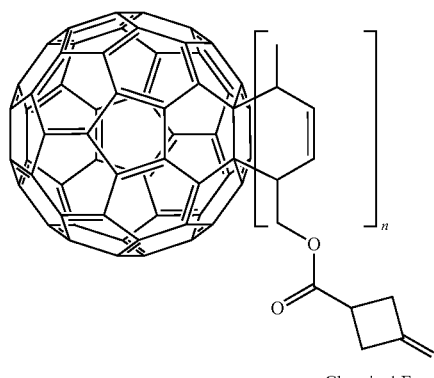
Chemical Formula 1-1-11
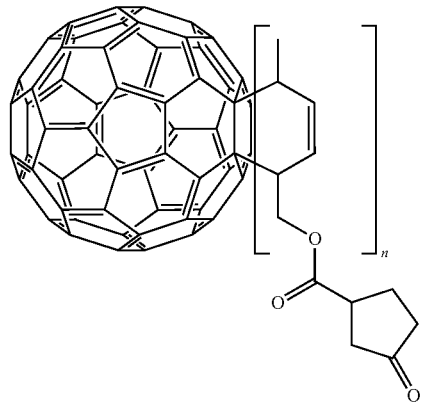
Chemical Formula 1-1-12
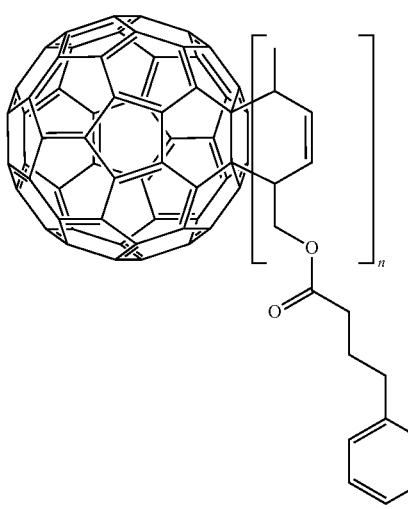
Chemical Formula 1-1-13
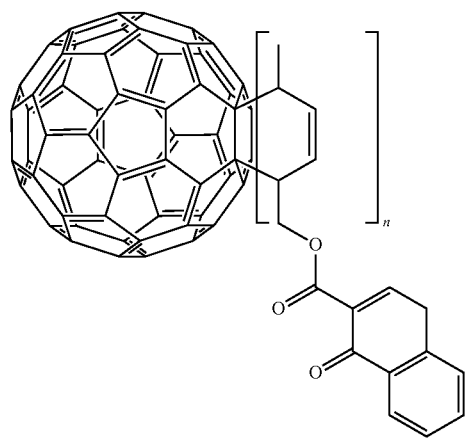
Chemical Formula 1-1-14
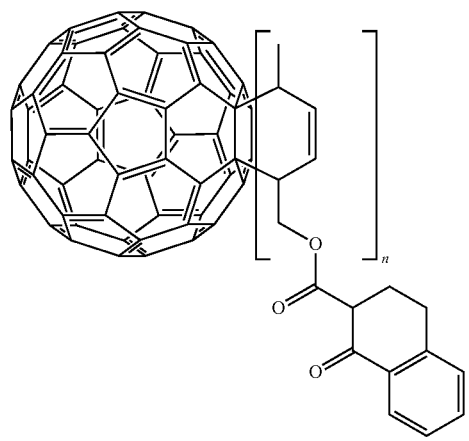
Chemical Formula 1-1-15
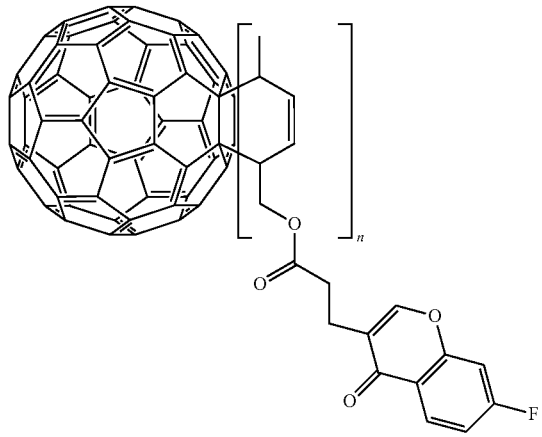

Chemical Formula 1-1-16
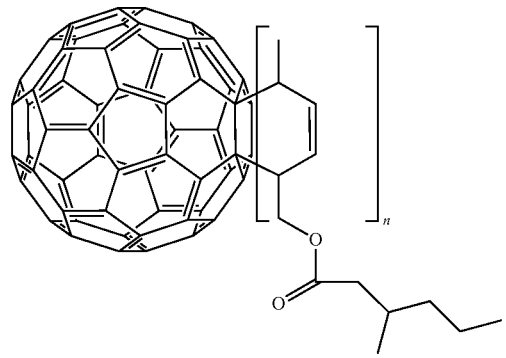
Chemical Formula 1-1-17
Chemical Formula 1-1-18
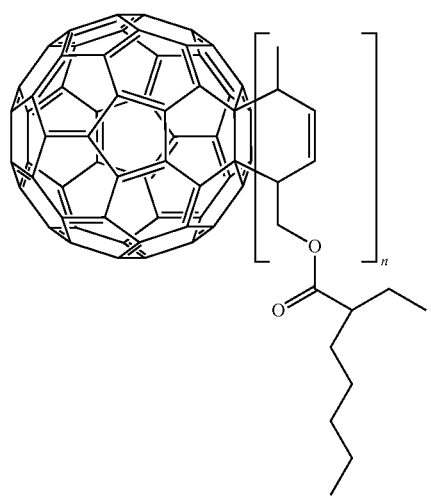
Chemical Formula 1-1-19
Chemical Formula 1-1-20
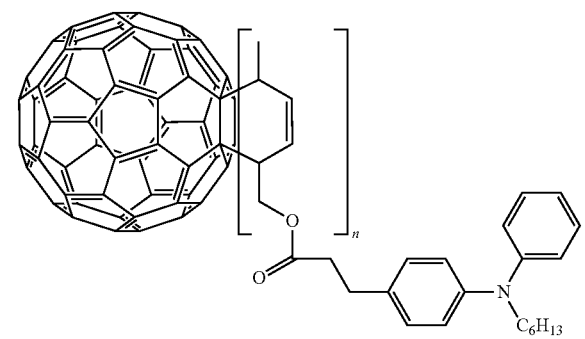
Chemical Formula 1-1-21
Chemical Formula 1-1-22
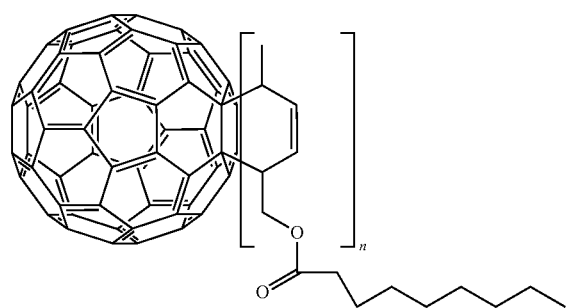
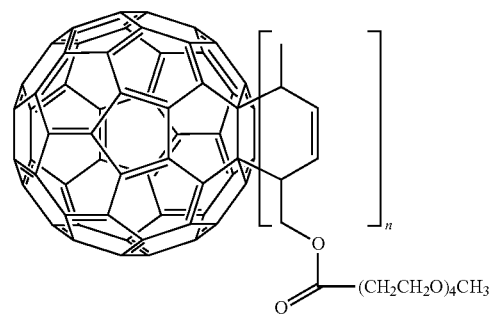
Chemical Formula 1-1-23
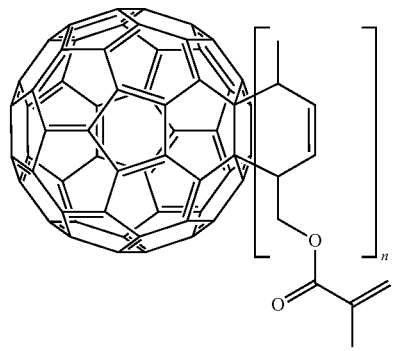

Chemical Formula 1-1-24
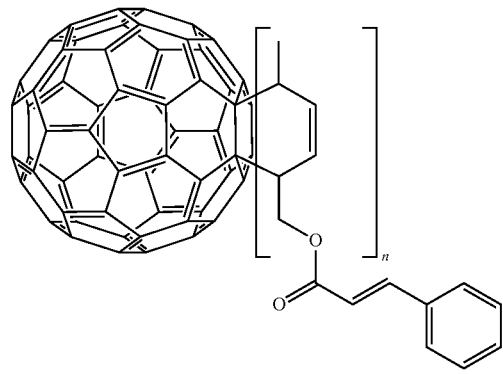
Chemical Formula 1-1-25
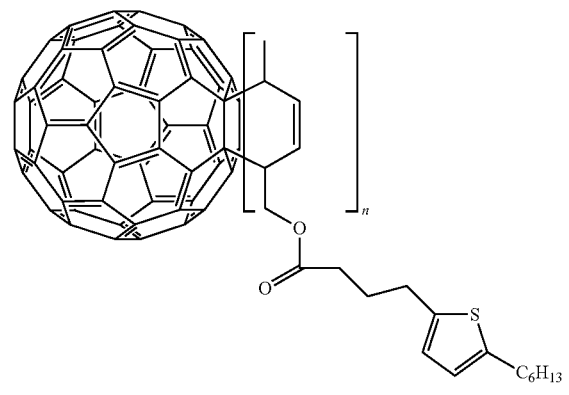
Chemical Formula 1-1-26
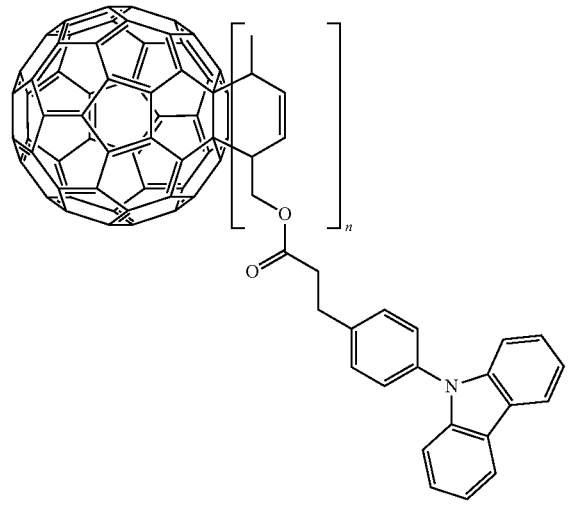
Chemical Formula 1-1-27
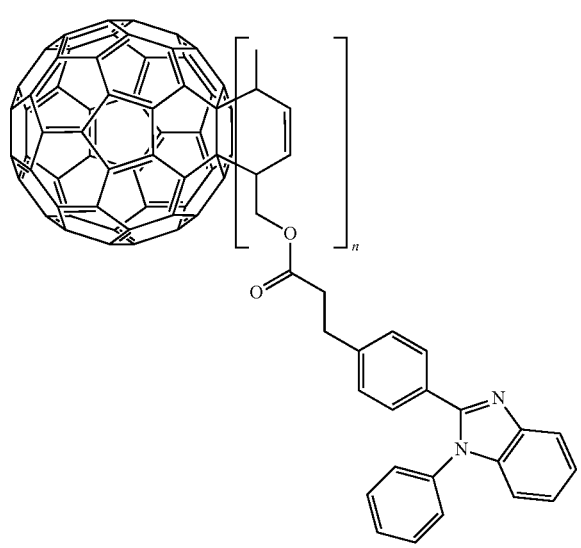
Chemical Formula 1-1-28
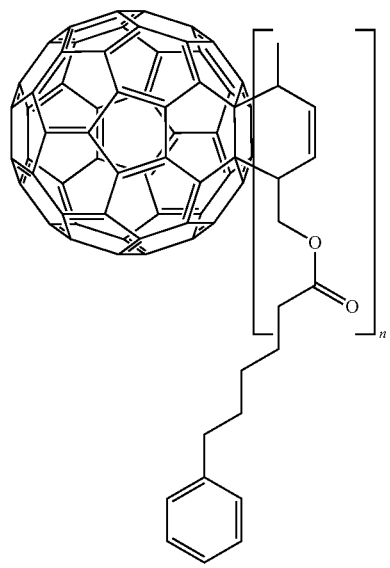

-continued

Chemical Formula 1-1-29

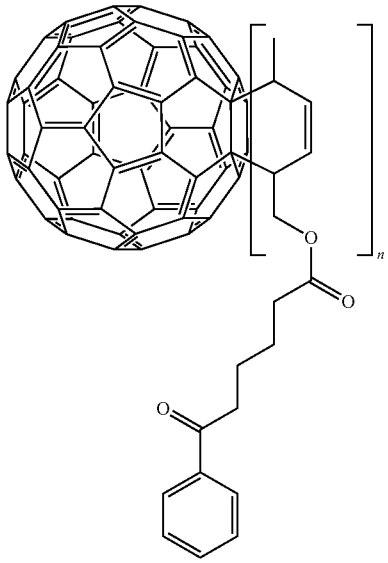

Chemical Formula 1-1-30

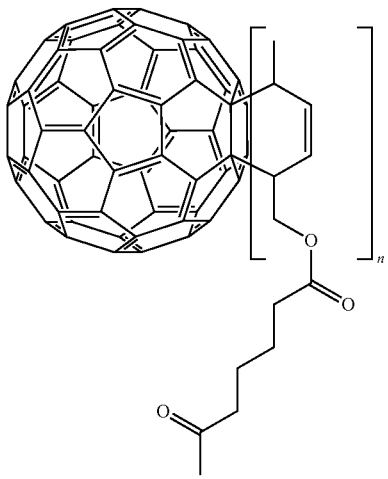

Chemical Formula 1-1-31

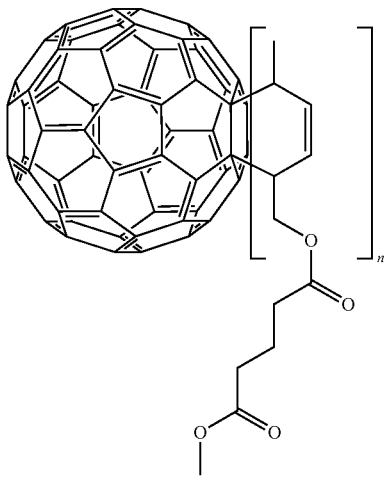

In Chemical Formulae 1-1-1 to 1-1-31, the definition of n is the same as n defined in Chemical Formula 1.

The fullerene derivative according to one embodiment of the present specification may further include other structures in addition to the structure within the parenthesis in Chemical Formula 1.

In one embodiment of the present specification, the fullerene skeleton of the fullerene derivative may be used either alone, or two or more types may be used together in any combination and ratio.

In one embodiment of the present specification, the fullerene derivative represented by Chemical Formula 1 may be prepared based on the preparation examples described below.

In the present specification, a fullerene derivative including a structure including cyclohexane may be prepared by conjugated diene and fullerene bonding through a Diels-Alder reaction.

By modifying a substituent of the conjugated diene, the fullerene derivative represented by Chemical Formula 1 as well as the fullerene derivatives of Chemical Formulae 1-1-1 to 1-1-27 may be prepared.

The present specification provides an organic electronic device including a first electrode; a second electrode provided opposite to the first electrode; and one or more organic material layers provided between the first electrode and the second electrode, wherein one or more layers of the organic material layers include the fullerene derivative described above.

In one embodiment of the present specification, the organic electronic device is selected from the group consisting of an organic light emitting device; an organic solar cell; and an organic transistor.

In one embodiment of the present specification, the organic electronic device may be an organic light emitting device.

One embodiment of the present specification provides an organic electronic device as an organic light emitting device including a first electrode, a second electrode, and one or more organic material layers disposed between the first electrode and the second electrode, wherein one or more layers of the organic material layers include the fullerene derivative.

In one embodiment of the present specification, the organic material layer includes a light emitting layer, and the light emitting layer includes the fullerene derivative.

In one embodiment of the present specification, the organic material layer includes a hole injection layer or a hole transfer layer, and the hole injection layer or the hole transfer layer includes the fullerene derivative.

In another embodiment of the present specification, the organic material layer includes an electron injection layer or an electron transfer layer, and the electron injection layer or the electron transfer layer includes the fullerene derivative.

In one embodiment of the present specification, the organic electronic device may be an organic transistor.

One embodiment of the present specification provides an organic electronic device as an organic transistor including a source, a drain, a gate and one or more organic material layers, wherein one or more layers of the organic material layers include the fullerene derivative.

In one embodiment of the present specification, the organic electronic device may be an organic solar cell.

In one embodiment of the present specification, the organic electronic device is an organic solar cell including a first electrode; a second electrode provided opposite to the first electrode; and one or more organic material layers provided between the first electrode and the second electrode, wherein one or more layers of the organic material layers include the fullerene derivative.

A principle of an organic solar cell is that a p-type semiconductor forms excitons paired with holes and electrons by light excitation, and the excitons are separated into electrons and holes at a p-n junction. The separated electrons and holes are transferred to an n-type semiconductor thin film and a p-type semiconductor thin film, respectively, and are collected in a first electrode and a second electrode, respectively, and as a result, the organic solar cell may be used as an electric energy externally.

FIG. 1 is a diagram illustrating an organic solar cell according to one embodiment of the present specification. In FIG. 1, the organic solar cell includes a substrate (101), a first electrode (102), a hole transfer layer (103), a photoactive layer (104) and a second electrode (105).

In one embodiment of the present specification, the organic material layer includes a photoactive layer, and an organic material layer provided between the photoactive layer and the first electrode or the second electrode, and the organic material layer provided between the photoactive layer and the first electrode or the second electrode includes the fullerene derivative.

In one embodiment of the present specification, the organic material layer includes a photoactive layer, the photoactive layer has a bilayer structure including an n-type organic material layer and a p-type organic material layer, and the n-type organic material layer includes the fullerene derivative.

In one embodiment of the present specification, the organic material layer includes a photoactive layer, the photoactive layer includes an electron donor material and an electron acceptor material, and the electron acceptor material includes the fullerene derivative.

In one embodiment of the present specification, the electron donor material and the electron acceptor material in the organic solar cell form a bulk heterojunction (BHJ).

A Bulk heterojunction means an electron donor material and an electron acceptor material being mixed together in a photoactive layer.

In one embodiment of the present specification, the electron acceptor material includes the fullerene derivative that is not heat cured or UV cured.

The fullerene derivative according to one embodiment of the present specification may be used as it is without heat curing or UV curing.

The electron acceptor material including the fullerene derivative represented by Chemical Formula 1 according to one embodiment of the present specification may be applied to a photoactive layer as it is without heat curing or UV curing. Therefore, the process has advantages in terms of time and/or costs.

In one embodiment of the present specification, the electron acceptor material includes the fullerene derivative that is heat cured or UV cured as necessary.

In one embodiment, the electron acceptor material may form a new matrix with an electron donor material through UV or heat curing.

In another embodiment, a new matrix may be formed between the electron acceptor materials through UV or heat curing.

In one embodiment of the present specification, the n-type organic material layer and/or the electron donor material are preferably compatible with a light absorption wavelength range or a spectrum within sunlight, preferably has a strong light absorbancy, and has excellent electrical properties such as charge mobility.

In one embodiment of the present specification, the electron donor material includes an organic compound, and the organic compound is an organic compound capable of being used in a solution process.

In one embodiment of the present specification, the n-type organic material layer and/or the electron donor material include an organic compound, and the organic compound includes a polymer compound or a monomer compound.

Specifically, the electron donor material includes the following structures including poly(phenylene vinylene) (PPV)-based polymers or poly(3-hexylthiophene) (P3HT)-based polymers.

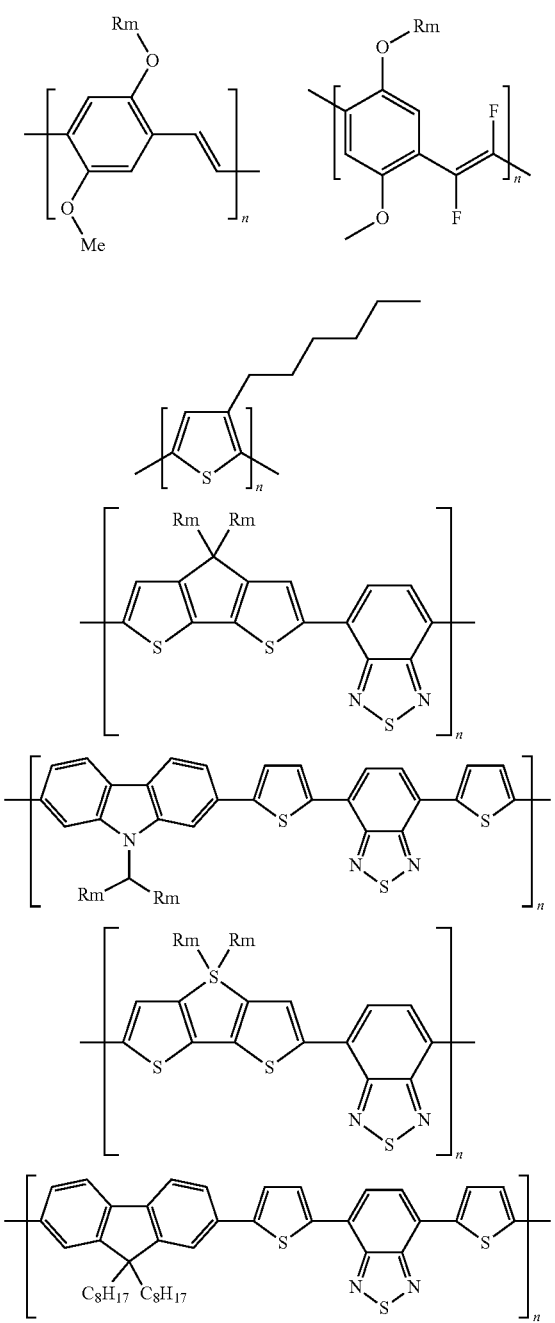

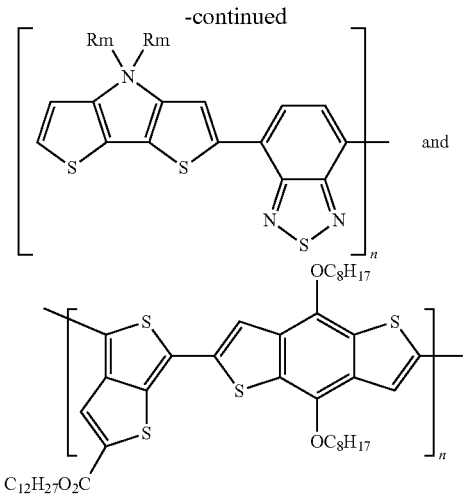

n is an integer of 1 to 1,000,

Rm is hydrogen, a substituted or unsubstituted alkyl group; a substituted or unsubstituted cycloalkyl group; a substituted or unsubstituted alkoxy group; a substituted or unsubstituted alkenyl group; a substituted or unsubstituted aromatic or aliphatic heteroring group including one or more of N, O and S atoms, or a substituted or unsubstituted aryl group.

The electron donor materials are preferably materials having a small band gap so as to absorb all visible ray regions within sunlight, and are generally polymer compounds, but are not limited thereto, and monomer compounds may be used.

The electron donor material and the electron acceptor material are mixed in a ratio of 1:100 to 100:1 (w/w). After the electron donor material and the electron acceptor material are mixed, the result may be annealed for 1 second to 24 hours at 30° C. to 300° C. in order to maximize the properties.

In one embodiment of the present specification, the thickness of the photoactive layer is from 10 nm to 10,000 nm.

In one embodiment of the present specification, the organic material layer includes a photoactive layer; and an organic material layer provided between the photoactive layer and the first electrode or the second electrode, and the organic material layer provided between the photoactive layer and the first electrode or the second electrode includes the fullerene derivative.

In one embodiment of the present specification, in the organic material layers, the organic material layer provided between the photoactive layer and the first electrode or the second electrode includes the fullerene derivative, and the fullerene derivative is an electron acceptor material and an electron transfer material.

In one embodiment of the present specification, in the organic material layers, the organic material layer provided between the photoactive layer and the first electrode or the second electrode includes a metal oxide, an organic material layer is provided between the metal oxide layer and the photoactive layer, and the organic material layer includes the fullerene derivative.

In one embodiment of the present specification, the organic material layer including the fullerene derivative contact with the metal oxide layer.

In one embodiment of the present specification, the organic material layer provided between the photoactive layer and the first electrode or the second electrode includes the fullerene derivative, and the fullerene derivative is an electron injection material.

In one embodiment of the present specification, the organic electronic device has a normal structure.

In one embodiment of the present specification, the organic electronic device has an inverted structure.

In one embodiment of the present specification, the organic electronic device has a normal structure, and the organic material layer includes a photoactive layer; and an organic material layer provided between the photoactive layer and the second electrode, wherein the organic material layer provided between the photoactive layer and the second electrode includes the fullerene derivative, and the first electrode is an anode electrode and the second electrode is a cathode electrode.

In one embodiment of the present specification, the organic electronic device has an inverted structure, and the organic material layer includes an organic material layer provided between the photoactive layer and the second electrode, wherein the organic material layer provided between the photoactive layer and the second electrode includes the fullerene derivative, and the first electrode is an anode electrode and the second electrode is a cathode electrode.

In one embodiment of the present specification, the first electrode may be an anode electrode or a cathode electrode. In addition, the second electrode may be a cathode electrode or an anode electrode.

In one embodiment of the present specification, the organic solar cell may have an arrangement in order of an anode electrode, a photoactive layer and a cathode electrode.

In another embodiment, the organic solar cell may also have an arrangement in order of a cathode electrode, a photoactive layer and an anode electrode, but the arrangement is not limited thereto.

In another embodiment, the organic solar cell may also have an arrangement in order of an anode electrode, a hole transfer layer, a photoactive layer, an electron transfer layer and a cathode electrode, or have an arrangement in order of a cathode electrode, an electron transfer layer, a photoactive layer, a hole transfer layer and an anode electrode, however, the arrangement is not limited thereto.

In another embodiment, the organic solar cell may also have an arrangement in order of an anode electrode, a buffer layer, a photoactive layer and a cathode electrode.

The organic solar cell of the present specification may be prepared using materials and methods known in the art except that the fullerene derivative represented by Chemical Formula 1 is included in one or more layers of the organic material layers of the organic solar cell.

One embodiment of the present specification provides a method for fabricating an organic solar cell including preparing a substrate; forming a first electrode on the top of the substrate; forming one or more organic material layers including a photoactive layer on the top of the first electrode; and forming a second electrode on the top of the organic material layers, wherein one or more layers of the organic material layers include the fullerene derivative.

The fullerene derivative may be included in the hole transfer layer; the photoactive layer; and/or the electron transfer layer.

For example, the organic solar cell according to the present invention may be fabricated by forming an anode by depositing or solution coating a metal, a metal oxide having conductivity, or alloys thereof using a physical vapor deposition (PVD) method such as sputtering or e-beam evaporation, or a solution coating method, forming an organic material layer thereon using a vacuum deposition or solution coating method, and then depositing a material that can be used as a cathode thereon.

Each layer of the organic material layers described above may be prepared using a solution process instead of a deposition method using various unimolecular or polymer materials, and examples of the solution process include roll to roll, spin coating, dip coating, casting, roll court, flow coating, doctor blading, screen printing, ink jet printing, gravure printing, offset printing, spray coating, a thermal printing method or the like.

Each layer of the organic material layers described above may be prepared using a method including dry film-forming methods such as vacuum deposition, sputtering, plasma and ion plating.

In one embodiment of the present specification, the method may include steps of depositing an anode, laminating a photoactive layer, arraying the photoactive layer, heat treating the photoactive layer and depositing a cathode.

The step of laminating a photoactive layer may be disposed in a composite thin film structure in which a solution mixed with an electron donor material and an electron acceptor material is sprayed and deposited on the upper side of both electrodes, that is, in a bulk heterojunction.

As the electron acceptor material, a mixed solution in which a composite polymer material is dissolved in an organic solvent may be used, and the electron acceptor material may include the fullerene derivative described above.

In one embodiment of the present specification, the fullerene derivative and P3HT are dissolved in an organic solvent and used.

The substrate in the present specification may include a glass substrate or a transparent plastic substrate, which has excellent transparency, surface smoothness, handling easiness and water resistance, but is not limited thereto, and substrates typically used in organic solar cells may be used without limit. Specific examples thereof include glass, polyethylene terphthalate (PET), polyethylene naphthalate (PEN), polypropylene (PP), polyimide (PI), triacetyl cellulose (TAC) and the like, but are not limited thereto.

The anode electrode may include a material that is transparent and has excellent conductivity, but the material is not limited thereto. Examples of the anode material include metals such as vanadium, chromium, copper, zinc or gold, or alloys thereof; metal oxides such as zinc oxide, indium oxide, indium tin oxide (ITO), molybdenum oxide or indium zinc oxide (IZO); a combination of metals and oxides such as ZnO:Al or $SnO_2$:Sb; conductive polymers such as poly (3-methylthiophene), poly[3,4-(ethylene-1,2-dioxy)thiophene] (PEDOT), polypyrrole and polyaniline, and the like, but are not limited thereto.

The method of forming an anode electrode is not particularly limited, however, the anode electrode may be formed by being applied to one surface of a substrate or coated in the form of a film using methods such as sputtering, E-beam, thermal deposition, spin coating, screen printing, ink jet printing, doctor blade or gravure printing.

When the anode electrode is formed on a substrate, the result may go through processes of cleaning, moisture removing and modifying to be hydrophilic.

For example, after a patterned ITO substrate is cleaned with a cleaning agent, acetone and isopropyl alcohol (IPA) in consecutive order, the ITO substrate is dried for 1 minute to 30 minutes at 100° C. to 150° C. and preferably for 10 minutes at 120° C. on a heating plate in order to remove moisture, and when the substrate is completely cleaned, the surface of the substrate is modified to be hydrophilic.

Through such surface modification, the junctional surface potential may be maintained at a level suitable for the surface potential of a photoactive layer. In addition, when the surface is modified, a polymer thin film may be readily formed on an anode electrode, and the quality of the thin film may be improved.

Preprocessing technologies for an anode electrode include a) a surface oxidation method using parallel plate discharge, b) a method of oxidizing the surface through the ozone generated by UV rays in a vacuum, c) an oxidation method using oxygen radicals generated by plasma, and the like.

One of the methods described above may be selected depending on the condition of an anode electrode or a substrate. However, it is commonly preferable to prevent the leave of the oxygen of the anode electrode or the surface of the substrate and to suppress the remaining of moisture and organic materials as much as possible, no matter which method is used. In this case, practical effects of the preprocessing may be maximized.

As a specific example, a method of oxidizing the surface through the ozone generated by UV rays may be used. Herein, a patterned ITO substrate may be fully dried by baking the patterned ITO substrate on a hot plate after being ultrasonic cleaned, and the patterned ITO substrate may be introduced into a chamber and then cleaned by the ozone generated by reacting the oxygen gas with UV light using a UV lamp.

However, the method of surface modification of a patterned ITO substrate in the present specification is not particularly limited, and any method oxidizing a substrate may be used.

The cathode electrode may include a metal having small work function, but is not limited thereto. Specific examples thereof include metals such as magnesium, calcium, sodium, potassium, titanium, indium, yttrium, lithium, gadolinium, aluminum, silver, tin and lead, or alloys thereof; or multilayer structure materials such as LiF/Al, $LiO_2$/Al, LiF/Fe, Al:Li, Al:$BaF_2$ and Al:$BaF_2$:Ba, but are not limited thereto.

The cathode electrode may be formed by being deposited inside a thermal depositor having a vacuum degree of $5\times10^{-7}$ torr or less, but the formation is not limited to this method.

The hole transfer layer and/or the electron transfer layer material play the role of efficiently transferring the electrons and the holes separated in a photoactive layer to an electrode, and the material is not particularly limited.

The hole transfer layer material may include poly(3,4-ethylenediocythiophene) doped with poly(styrenesulfonic acid) (PEDOT:PSS), molybdenum oxide ($MoO_x$); vanadium oxide ($V_2O_5$); nickel oxide (NiO); tungsten oxide ($WO_x$), and the like, but is not limited thereto.

The electron transfer layer material may include electron-extracting metal oxides, and may specifically include a metal complex of 8-hydroxyquinoline; a complex including $Alq_3$; a metal complex including Liq; LiF; Ca; titanium oxide ($TiO_x$); zinc oxide (ZnO); cesium carbonate ($Cs_2CO_3$), and the like, but is not limited thereto.

The photoactive layer may be formed by dissolving a photoactive material such as an electron donor and/or an electron acceptor in an organic solvent, and then applying the solution using a method such as spin coating, dip coating, screen printing, spray coating, doctor blade and brush painting, but the method is not limited thereto.

Hereinafter, a method for preparing the fullerene derivative and a method for fabricating an organic solar cell using

Preparation Example 1-1-1

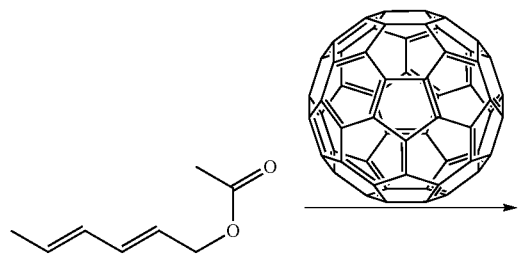

Chemical Formula 1-A-1

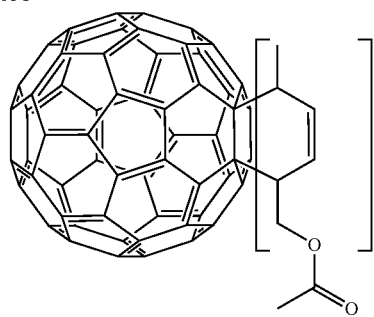

Chemical Formula 1-1-1

2,4-hexadienyl acetate (1.4 g, 10.0 mmol) and $C_{60}$ (7.2 g, 10.0 mmol) were stirred for 28 hours at 110° C. After the reaction, the temperature was lowered to room temperature and excess 1,2-dichlorobenznene (OD) was removed under vacuum. After the concentrated mixture was column purified (toluene:n-Hex), a liquid obtained after concentrating the solvent was recrystallized using toluene and hexane, and then the result was filtered and dried to obtain 930 mg of a fullerene derivative of Chemical Formula 1-1-1 in which n=1 (yield 10.8%, HPLC purity 99.9% up).

Preparation Example 1-1-2

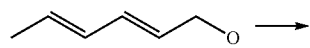

Chemical Formula 1-A-2

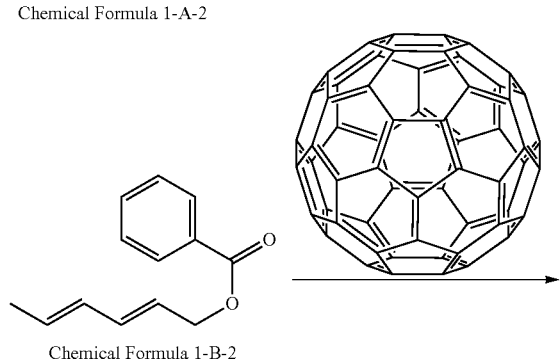

Chemical Formula 1-B-2

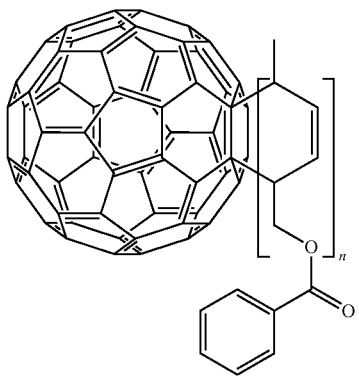

Chemical Formula 1-1-2

After 2,4-hexadien-1-ol (1.96 g, 20.0 mmol) was dissolved in 80 mL of anhydrous tetrahydrofuran (THF), 10 mL of benzoyl chloride and 5 mL of triethylamine were added thereto, and the result was stirred for 5 hours at room temperature. The layer was separated by adding distilled water and ethyl ether, and the organic material layer was extracted.

The organic material layer was dried using anhydrous magnesium sulfate, and then was filtered and vacuum distilled to obtain a liquid compound, and the liquid compound was purified through column chromatography to obtain (2E,4E)-hexa-2,4-dien-1-yl benzoate of Chemical Formula 1-B-2 (2.74 g, 98%).

0.56 g of a fullerene derivative of Chemical Formula 1-1-2 in which n=1 (yield 8.8%) was obtained in the same manner as in Preparation Example 1-1-1, except that Chemical Formula 1-B-2 (1.4 g, 6.92 mmol) was used instead of Chemical Formula 1-A-1.

In addition, 2.2 g of a fullerene derivative of Chemical Formula 1-1-2 in which n=1 or greater was obtained in the same manner as in Preparation Example 1-1-1, except that Chemical Formula 1-B-2 (2.8 g, 20 mmol) was used instead of Chemical Formula 1-A-1, and $C_{60}$ (3.6 g, 5 mmol) was used.

Preparation Example 1-1-3

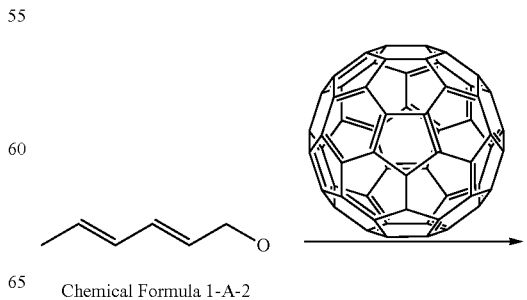

Chemical Formula 1-A-2

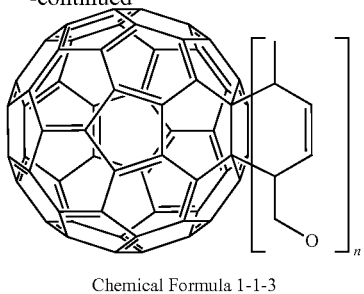

Chemical Formula 1-1-3

3.1 g of Chemical Formula 1-1-3 in which n=1 or greater was obtained in the same manner as in Preparation Example 1-1-1, except that Chemical Formula 1-A-2 (1.96 g, 20 mmol) was used instead of Chemical Formula 1-A-1, and $C_{60}$ (3.6 g, 5 mmol) was used.

Preparation Example 1-1-4

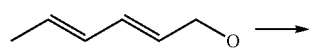

Chemical Formula 1-A-2

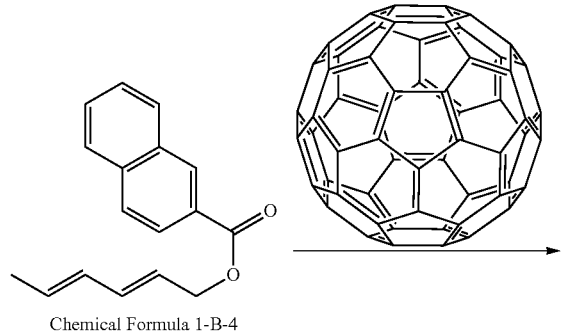

Chemical Formula 1-B-4

↓

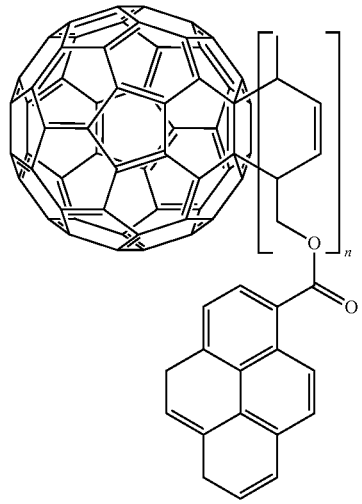

Chemical Formula 1-1-4

Chemical Formula 1-B-4 was prepared in the same manner as Chemical Formula 1-B-2 of Preparation Example 1-1-2, except that naphthalene-2-carbonyl chloride was used instead of benzoyl chloride.

0.87 g of Chemical Formula 1-1-4 in which n=1 (yield 5.1%) was obtained in the same manner as in Preparation Example 1-1-1, except that Chemical Formula 1-B-4 (1.26 g, 5 mmol) was used instead of Chemical Formula 1-A-1, and $C_{60}$ (3.6 g, 5 mmol) was used.

Preparation Example 1-1-5

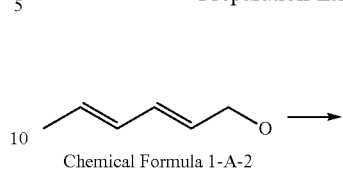

Chemical Formula 1-A-2

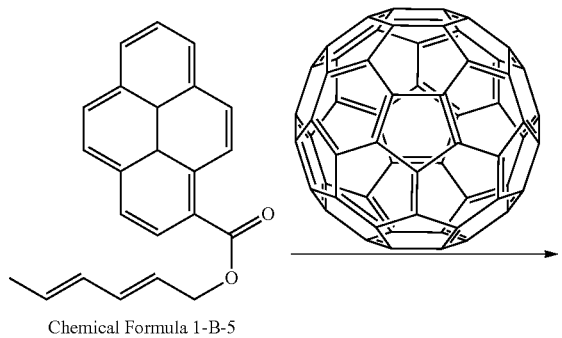

Chemical Formula 1-B-5

↓

Chemical Formula 1-1-5

Chemical Formula 1-B-5 was prepared in the same manner as Chemical Formula 1-B-2 of Preparation Example 1-1-2, except that pyrene-1-carbonyl chloride was used instead of benzoyl chloride.

0.29 g of Chemical Formula 1-1-5 in which n=1 (yield 5.5%) was obtained in the same manner as in Preparation Example 1-1-1, except that Chemical Formula 1-B-5 (1.64 g, 5 mmol) was used instead of Chemical Formula 1-A-1, and $C_{60}$ (3.6 g, 5 mmol) was used.

Preparation Example 1-1-6

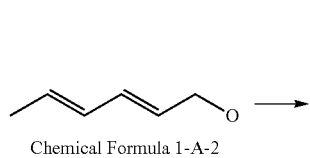

Chemical Formula 1-A-2

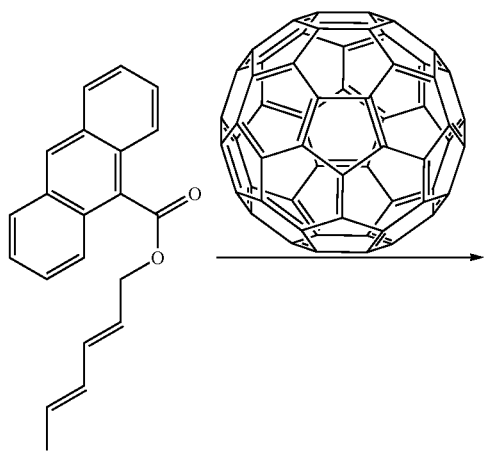

Chemical Formula 1-B-6

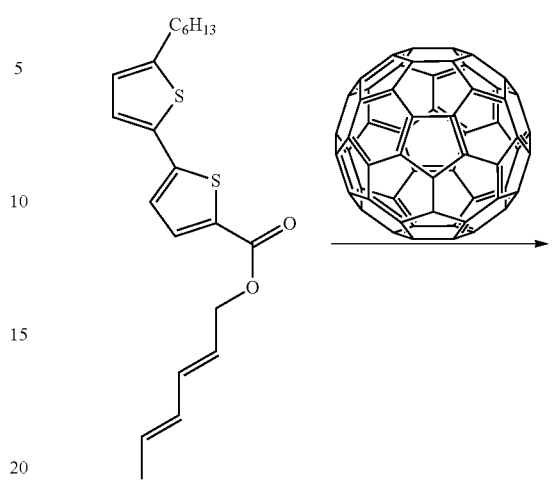

Chemical Formula 1-B-7

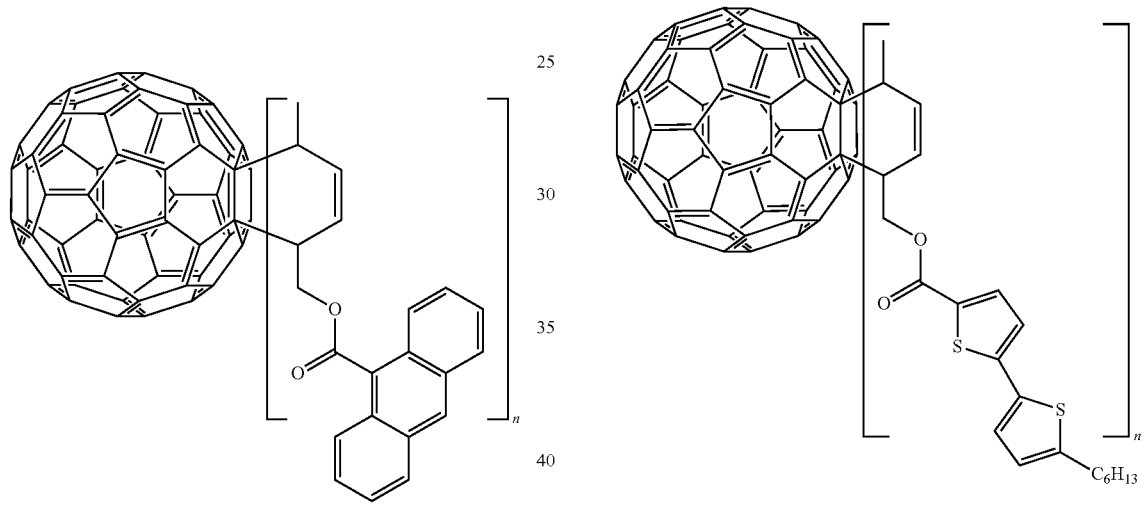

Chemical Formula 1-1-6

Chemical Formula 1-1-7

Chemical Formula 1-B-6 was prepared in the same manner as Chemical Formula 1-B-2 of Preparation Example 1-1-2, except that anthracene-9-carbonyl chloride was used instead of benzoyl chloride.

0.74 g of Chemical Formula 1-1-6 in which n=1 (yield 6.94%) was obtained in the same manner as in Preparation Example 1-1-1, except that Chemical Formula 1-B-6 (1.51 g, 5 mmol) was used instead of Chemical Formula 1-A-1, and $C_{60}$ (3.6 g, 5 mmol) was used.

Preparation Example 1-1-7

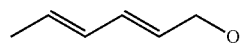

Chemical Formula 1-A-2

Chemical Formula 1-B-7 in which n=1 was prepared in the same manner as Chemical Formula 1-B-2 of Preparation Example 1-1-2, except that (2E,4E)-hexa-2,4-dien-1-yl 5'-hexyl-[2,2'-bithiophene]-5-carboxylate was used instead of benzoyl chloride.

1.38 g of Chemical Formula 1-1-7 in which n=1 (yield 12%) was obtained in the same manner as in Preparation Example 1-1-1, except that Chemical Formula 1-B-7 (1.56 g, 5 mmol) was used instead of Chemical Formula 1-A-1, and $C_{60}$ (3.6 g, 5 mmol) was used.

Preparation Example 1-1-8

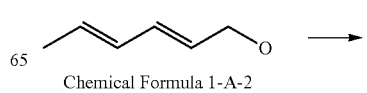

Chemical Formula 1-A-2

-continued

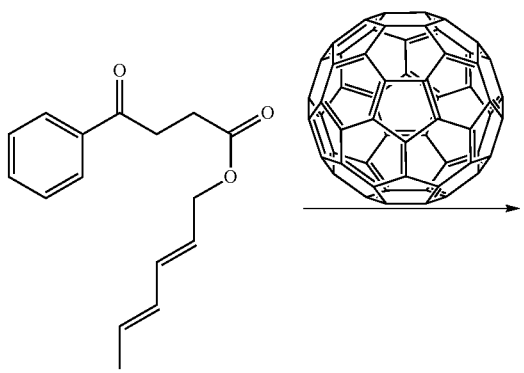

Chemical Formula 1-B-8

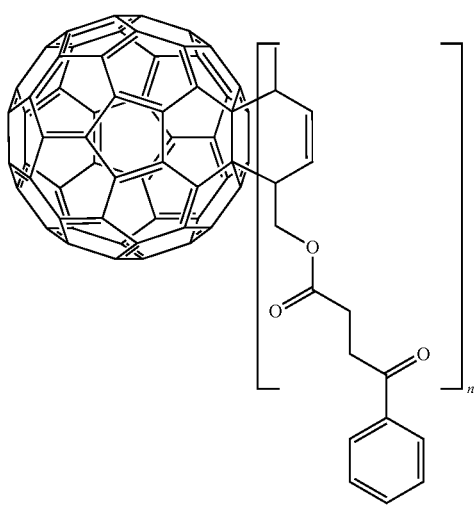

Chemical Formula 1-1-8

Chemical Formula 1-B-8 was prepared in the same manner as Chemical Formula 1-B-2 of Preparation Example 1-1-2, except that 4-oxo-4-phenylbutanoyl chloride was used instead of benzoyl chloride.

0.47 g of Chemical Formula 1-1-8 in which n=1 (yield 9.7%) was obtained in the same manner as in Preparation Example 1-1-1, except that Chemical Formula 1-B-8 (1.29 g, 5 mmol) was used instead of Chemical Formula 1-A-1, and $C_{60}$ (3.6 g, 5 mmol) was used.

Preparation Example 1-1-9

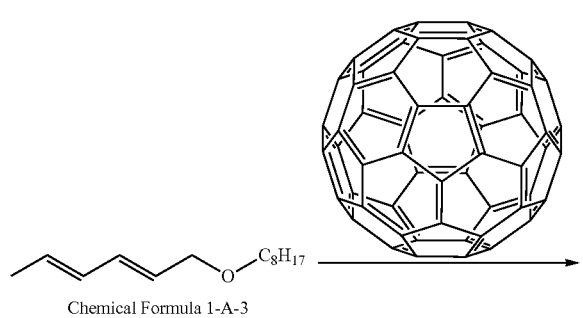

Chemical Formula 1-A-3

-continued

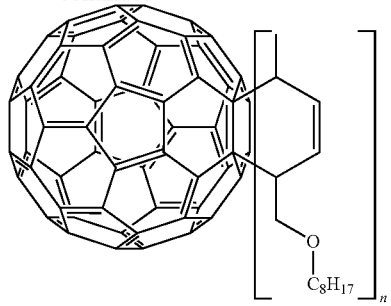

Chemical Formula 1-1-9

0.64 g of Chemical Formula 1-1-9 in which n=1 (yield 13.7%) was obtained in the same manner as in Preparation Example 1-1-1, except that Chemical Formula 1-A-3 (1.05 g, 5 mmol) was used instead of Chemical Formula 1-A-1, and $C_{60}$ (3.6 g, 5 mmol) was used.

Fabrication of Organic Solar Cell and Measurement of its Properties

Photoelectric conversion properties of organic solar cells of Preparation Example 1-1-1 to Preparation Example 1-1-9 were measured under the condition of 100 mW/cm$^2$ (AM 1.5), and the results are shown in the following Table 1.

Example 1-1

Fabrication of Organic Solar Cell

A composite solution was prepared by dissolving the compound prepared in Preparation Example 1-1-1 and P3HT in a ratio of 1:0.7 in chlorobenzene (CB). Herein, the concentration was adjusted to 2.0 wt %, and the structure of an organic solar cell employed an ITO/PEDOT:PSS/photoactive layer/Al structure. The glass substrate coated with ITO was ultrasonic cleaned using distilled water, acetone and 2-propanol, and after the ITO surface was ozone treated for 10 minutes, the surface was spin-coated with PEDOT:PSS (baytrom P) to a thickness of 45 nm, and then heat treated for 10 minutes at 120° C. In order to coat the photoactive layer, the compound-P3HT composite solution was filtered using a PP syringe filter of 0.45 μm, then spin-coated, and deposited with Al to a thickness of 200 nm using a thermal evaporator under the vacuum of 3×10$^{-8}$ torr, and as a result, an organic solar cell was fabricated.

Example 1-2

Fabrication of Organic Solar Cell

An organic solar cell was fabricated in the same manner as in Example 1-1, except that Chemical Formula 1-1-2 prepared in Preparation Example 1-1-2 was used instead of Chemical Formula 1-1-1, and the ratio of the P3HT and the fullerene derivative was 1:1.

Example 1-3

Fabrication of Organic Solar Cell

An organic solar cell was fabricated in the same manner as in Example 1-1, except that Chemical Formula 1-1-3 prepared in Preparation Example 1-1-3 was used instead of Chemical Formula 1-1-1, and the ratio of the P3HT and the fullerene derivative was 1:1.

Example 1-4

Fabrication of Organic Solar Cell

An organic solar cell was fabricated in the same manner as in Example 1-1, except that Chemical Formula 1-1-4 prepared in Preparation Example 1-1-4 was used instead of Chemical Formula 1-1-1, and the ratio of the P3HT and the fullerene derivative was 1:1.

Example 1-5

Fabrication of Organic Solar Cell

An organic solar cell was fabricated in the same manner as in Example 1-1, except that Chemical Formula 1-1-2 prepared in Preparation Example 1-1-5 was used instead of Chemical Formula 1-1-5, and the ratio of the P3HT and the fullerene derivative was 1:1.

Example 1-6

Fabrication of Organic Solar Cell

An organic solar cell was fabricated in the same manner as in Example 1-1, except that Chemical Formula 1-1-6 prepared in Preparation Example 1-1-6 was used instead of Chemical Formula 1-1-1, and the ratio of the P3HT and the fullerene derivative was 1:1.

Example 1-7

Fabrication of Organic Solar Cell

An organic solar cell was fabricated in the same manner as in Example 1-1, except that Chemical Formula 1-1-7 prepared in Preparation Example 1-1-7 was used instead of Chemical Formula 1-1-1, and the ratio of the P3HT and the fullerene derivative was 1:1.

Example 1-8

Fabrication of Organic Solar Cell

An organic solar cell was fabricated in the same manner as in Example 1-1, except that Chemical Formula 1-1-8 prepared in Preparation Example 1-1-8 was used instead of Chemical Formula 1-1-1, and the ratio of the P3HT and the compound of Chemical Formula 1-1-8 was 1:0.7.

Example 1-9

Fabrication of Organic Solar Cell

An organic solar cell was fabricated in the same manner as in Example 1-1, except that Chemical Formula 1-1-9 prepared in Preparation Example 1-1-9 was used instead of Chemical Formula 1-1-1, and the ratio of the P3HT and the fullerene derivative was 1:1.

Example 1-10

Fabrication of Organic Solar Cell

An organic solar cell was fabricated in the same manner as in Example 1-1, except that a polymer represented by the following Chemical Formula 1-2-1 and Chemical Formula 1-1-1 were prepared in 1:0.7.

<Chemical Formula 1-2-1>

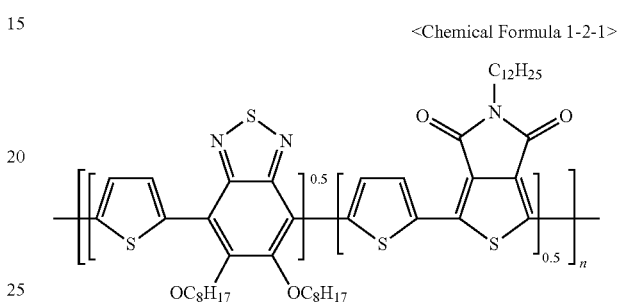

Comparative Example 1-1

Fabrication of Organic Solar Cell

A composite solution was prepared by dissolving P3HT and $PC_{61}BM$ in a ratio of 1:0.7 in 1,2-dichlorobenzene (DCB). Herein, the concentration was adjusted to 1.0 to 2.0 wt %, and an organic solar cell employed an ITO/PEDOT:PSS/photoactive layer/LiF/Al structure. The glass substrate coated with ITO was ultrasonic cleaned using distilled water, acetone and 2-propanol, and after the ITO surface was ozone treated for 10 minutes, the surface was spin-coated with PEDOT:PSS (baytrom P) to a thickness of 45 nm, and then heat treated for 10 minutes at 120° C. In order to coat the photoactive layer, the compound-PCBM composite solution was filtered using a PP syringe filter of 0.45 μm, then spin-coated, heat treated for 5 minutes at 120° C., and deposited with LiF to a thickness of 7 Å and then with Al to a thickness of 200 nm using a thermal evaporator under the vacuum of $3\times10^{-8}$ torr, and as a result, an organic solar cell was fabricated.

TABLE 1

| Active Layer (P3HT:Compound) | | $V_{OC}$ (V) | $J_{SC}$ (mA/cm$^2$) | FF | PCE (%) |
|---|---|---|---|---|---|
| Comparative Example 1-1 | P3HT:$PC_{61}BM$ = 1:0.7 | 0.65 | 7.71 | 0.59 | 2.91 |
| Example 1-1 | P3HT:Chemical Formula 1-1-1 = 1:0.7 | 0.63 | 8.90 | 0.54 | 3.03 |
| Example 1-2 | P3HT:Chemical Formula 1-1-2 = 1:1 | 0.64 | 7.41 | 0.62 | 2.76 |
| Example 1-3 | P3HT:Chemical Formula 1-1-3 = 1:1 | 0.63 | 7.32 | 0.57 | 2.62 |
| Example 1-4 | P3HT:Chemical Formula 1-1-4 = 1:1 | 0.69 | 4.73 | 0.30 | 0.98 |
| Example 1-5 | P3HT:Chemical Formula 1-1-5 = 1:1 | 0.63 | 7.72 | 0.66 | 3.21 |

TABLE 1-continued

| Active Layer (P3HT:Compound) | | $V_{OC}$ (V) | $J_{SC}$ (mA/cm²) | FF | PCE (%) |
|---|---|---|---|---|---|
| Example 1-6 | P3HT:Chemical Formula 1-1-6 = 1:1 | 0.65 | 7.69 | 0.63 | 3.15 |
| Example 1-7 | P3HT:Chemical Formula 1-1-7 = 1:1 | 0.620 | 9.16 | 0.42 | 2.38 |
| Example 1-8 | P3HT:Chemical Formula 1-1-8 = 1:0.7 | 0.67 | 8.98 | 0.65 | 3.91 |
| Example 1-9 | P3HT:Chemical Formula 1-1-9 = 1:1 | 0.64 | 7.89 | 0.54 | 2.73 |
| Example 1-10 | Chemical Formula 1-2-1:Chemical Formula 1-1-1 = 1:0.7 | 0.81 | 8.65 | 0.60 | 4.23 |

In Table 1, $V_{oc}$ means an open voltage, $J_{sc}$ means a short-circuit current, FF means a fill factor, and PCE means energy conversion efficiency. The open voltage and the short-circuit current are each an x-axis and a y-axis intercept in the four quadrants of a voltage-current density curve, and as these two values increase, solar cell efficiency is preferably enhanced. In addition, the fill factor is a value dividing the rectangle area that can be drawn inside the curve by a product of the short-circuit current and the open voltage. The energy conversion efficiency may be obtained when these three values are divided by the intensity of irradiated light, and it is preferable as the value is higher.

In the present specification, P3HT and Compound 1-2-1 were used as an electron donor material, however, the electron donor material is not limited thereto, and is not limited to polymer compounds or monomer compounds as long as it is a compound capable of being used in a solution process.

According to one embodiment of the present specification, the examples are provided for a device with a normal structure only, however, the examples may be provided for a device with an inverted structure as well.

While examples of the present invention have been described above, it will be apparent that the scope of the present invention is not limited thereto since these specific descriptions are provided to instruct the scope of the present invention for those skilled in the art. Therefore, the actual scope of the present invention is defined by the appended claims and their equivalents.

The invention claimed is:
1. A fullerene derivative of Chemical Formula 1:

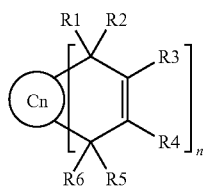

[Chemical Formula 1]

wherein:
n is an integer of 1 to 5;
when n is 2 or greater, structures within a parenthesis are the same as or different from each other;
Cn is fullerene of $C_{60}$ to $C_{120}$;
R1 to R6 are the same as or different from each other, and each is independently hydrogen, a halogen group, a nitro group, a cyano group, a carboxylic acid group, a hydroxyl group, a substituted or unsubstituted carbonyl group, a sulfo group (—SO₃H), a substituted or unsubstituted alkyl group, a substituted or unsubstituted alkoxy group, a substituted or unsubstituted cycloalkyl group, a substituted or unsubstituted alkenyl group, a substituted or unsubstituted ester group, a substituted or unsubstituted thioester group, a substituted or unsubstituted amide group, a substituted or unsubstituted ether group, a substituted or unsubstituted sulfonyl group (—SO₂—), a substituted or unsubstituted alkylthioxy group, a substituted or unsubstituted arylthioxy group, a substituted or unsubstituted alkylamine group, a substituted or unsubstituted arylamine group, a substituted or unsubstituted arylalkyl group, a substituted or unsubstituted heteroarylalkyl group, a substituted or unsubstituted aryl group, a substituted or unsubstituted heteroring group, or adjacent substituents bond to each other to form a substituted or unsubstituted hydrocarbon ring or a substituted or unsubstituted heteroring;
only one of R1 to R6 is

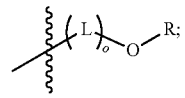

o is an integer of 1 to 3, and when o is an integer of 2 or greater, two or more Ls are the same as or different from each other;
L is an unsubstituted alkylene; and
R is hydrogen, a carboxylic acid group, a substituted or unsubstituted carbonyl group, an unsubstituted alkyl group, a substituted or unsubstituted cycloalkyl group, a substituted or unsubstituted alkenyl group, a substituted or unsubstituted ester group, a substituted or unsubstituted thioester group, a substituted or unsubstituted amide group, a substituted or unsubstituted sulfonyl group (—SO₂—), a substituted or unsubstituted arylalkyl group, a substituted or unsubstituted aryl group, or a substituted or unsubstituted heteroring group,
when R is a substituted carbonyl group substituted with a substituted alkyl group, the substituted alkyl group of the substituted carbonyl group is substituted with one or more substituents selected from the group consisting of a halogen group, a nitro group, a cyano group, a hydroxyl group, a carbonyl group, a sulfo group, an allyl group, an alkoxy group, a cycloalkyl group, an alkenyl group, an ester group, an ether group, a sulfonyl group, a sulfoxy group, an arylalkyl group, an aryl group, and a heteroring group,
wherein when one of R5 and R6 is unsubstituted alkyl and the other one of R5 and R6 is hydrogen, R3 and R4 are each hydrogen, one of R1 and R2 is hydrogen and the other one of R1 and R2 is

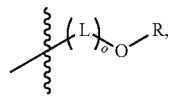

L is an unsubstituted alkylene, and o is 1, R is a carboxylic acid group, a substituted or unsubstituted carbonyl group, an unsubstituted alkyl group, a substituted or unsubstituted cycloalkyl group, a substituted or unsubstituted alkenyl group, a substituted or unsubstituted ester group, a substituted or unsubstituted thioester group, a substituted or unsubstituted amide group, a substituted or unsubstituted sulfonyl group (—SO$_2$—), a substituted or unsubstituted arylalkyl group, a substituted or unsubstituted aryl group, or a substituted or unsubstituted heteroring group.

2. The fullerene derivative of claim 1, wherein the fullerene derivative of Chemical Formula 1 is a fullerene derivative of Chemical Formula 2 or 3:

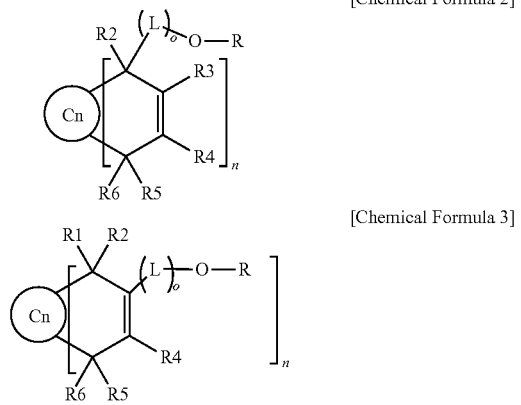

[Chemical Formula 2]

[Chemical Formula 3]

wherein
R, Cn, n, o, L and R1 to R6 are the same as for Chemical Formula 1.

3. The fullerene derivative of claim 1, wherein the fullerene derivative of Chemical Formula 1 is a fullerene derivative of Chemical Formula 2-1 or Chemical Formula 3-1:

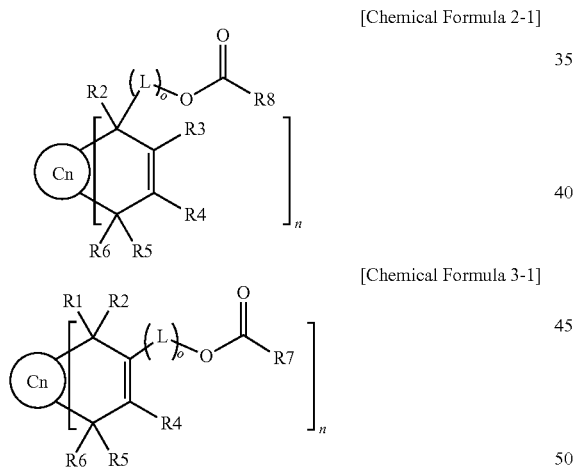

[Chemical Formula 2-1]

[Chemical Formula 3-1]

wherein:
Cn, n, o, L and R1 to R6 are the same as for Chemical Formula 1;
R7 and R8 are each independently hydrogen, a substituted or unsubstituted alkyl group, a substituted or unsubstituted cycloalkyl group, a substituted or unsubstituted alkenyl group, a substituted or unsubstituted ether group, a substituted or unsubstituted sulfonyl group, a substituted or unsubstituted arylalkyl group, substituted or unsubstituted cyclic ketone, a substituted or unsubstituted aryl group, or a substituted or unsubstituted heteroring group; and
when R8 is a substituted alkyl group, the substituted alkyl group is substituted with one or more substituents selected from the group consisting of a halogen group, a nitro group, a cyano group, a hydroxyl group, a carbonyl group, a sulfo group, an allyl group, an alkoxy group, a cycloalkyl group, an alkenyl group, an ester group, an ether group, a sulfonyl group, a sulfoxy group, an arylalkyl group, an aryl group, and a heteroring group.

4. The fullerene derivative of claim 1, wherein R is hydrogen, an unsubstituted alkyl group, or a substituted or unsubstituted carbonyl group.

5. The fullerene derivative of claim 3, wherein R7 and R8 are each independently a substituted or unsubstituted alkyl group, a substituted or unsubstituted alkenyl group, a substituted or unsubstituted aryl group, substituted or unsubstituted cyclic ketone, or a substituted or unsubstituted heteroring group.

6. The fullerene derivative of claim 1, wherein the fullerene derivative of Chemical Formula 1 is a fullerene derivative of Chemical Formulae 1-1-1, 1-1-2, and 1-1-4 to 1-1-30:

Chemical Formula 1-1-1

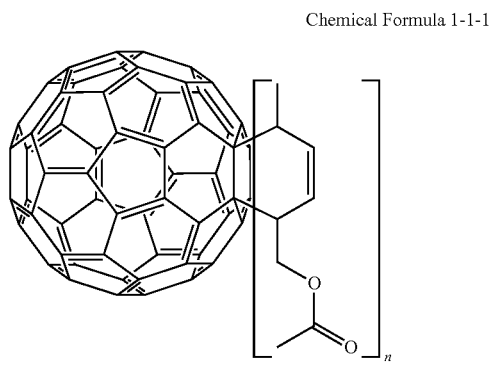

Chemical Formula 1-1-2

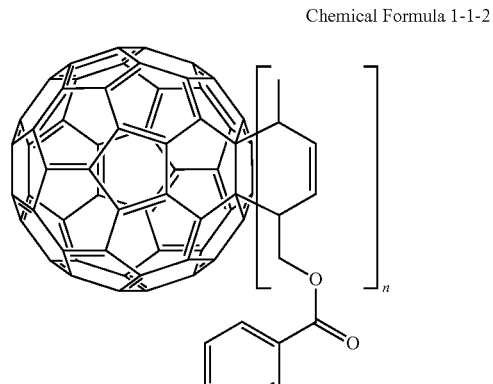

Chemical Formula 1-1-4

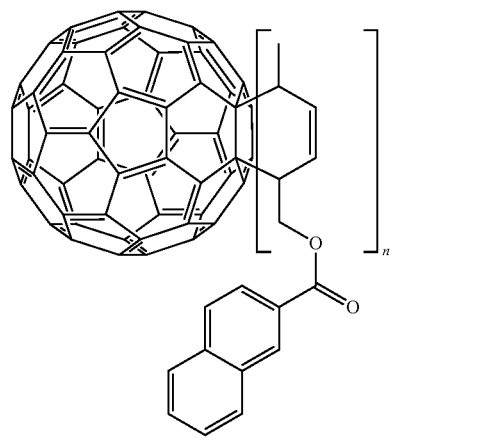

Chemical Formula 1-1-5
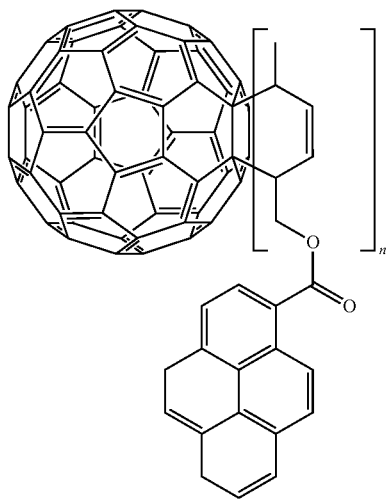
Chemical Formula 1-1-6
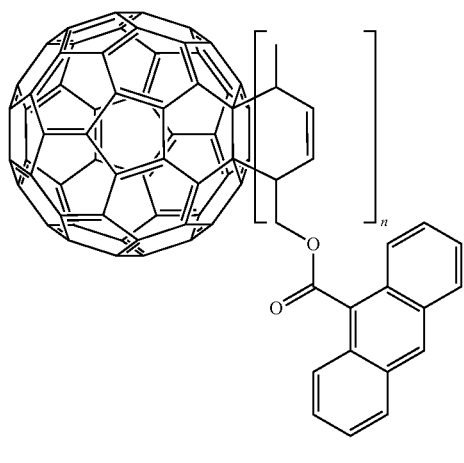
Chemical Formula 1-1-7
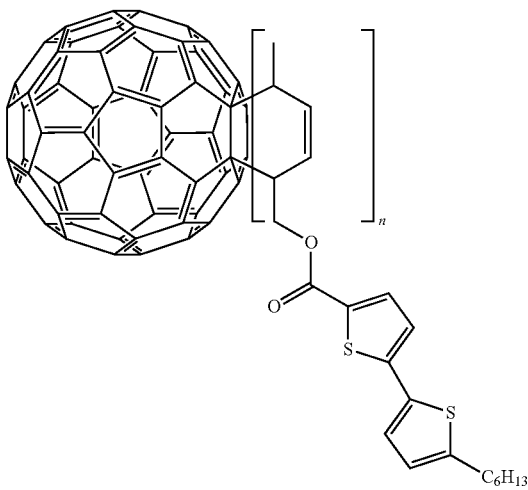
Chemical Formula 1-1-8
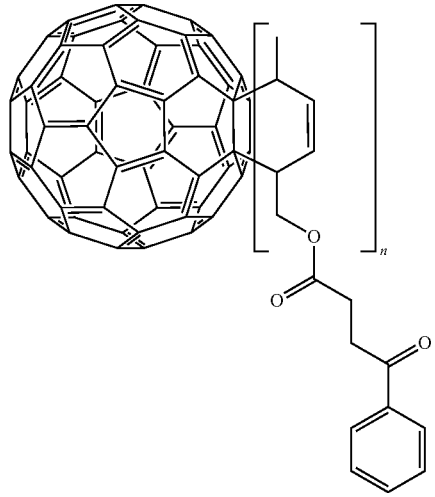
Chemical Formula 1-1-9
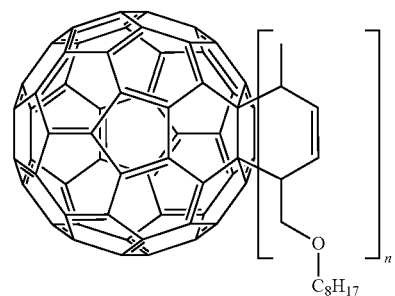
Chemical Formula 1-1-10
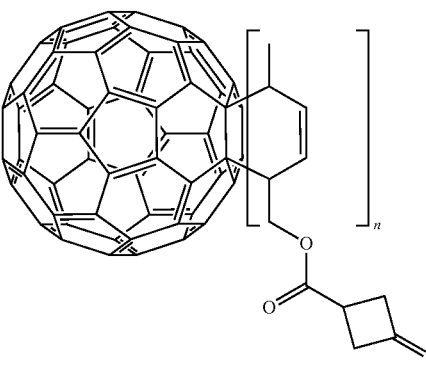
Chemical Formula 1-1-11
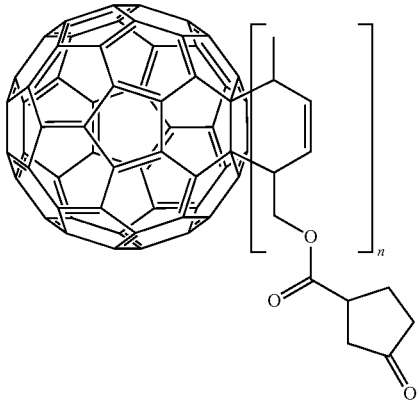

Chemical Formula 1-1-12
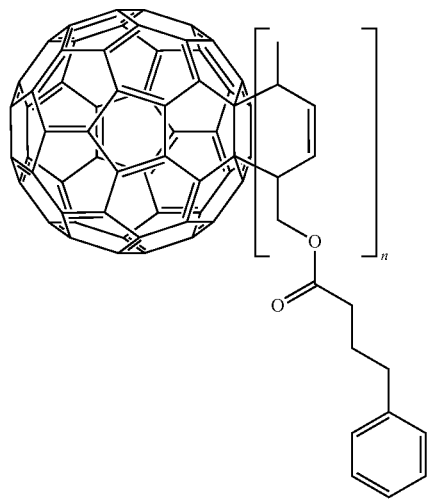
Chemical Formula 1-1-13
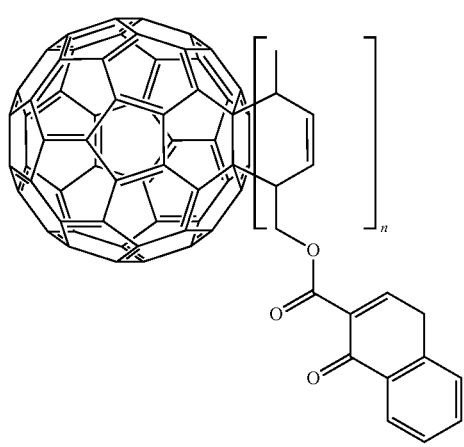
Chemical Formula 1-1-14
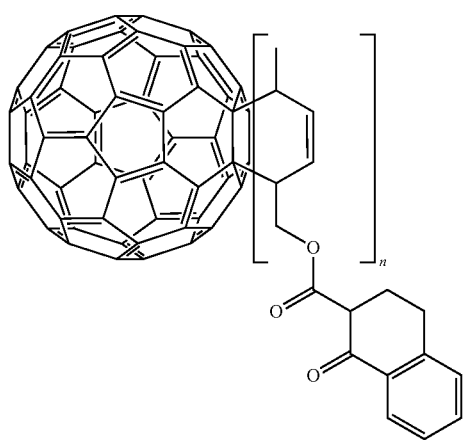
Chemical Formula 1-1-15
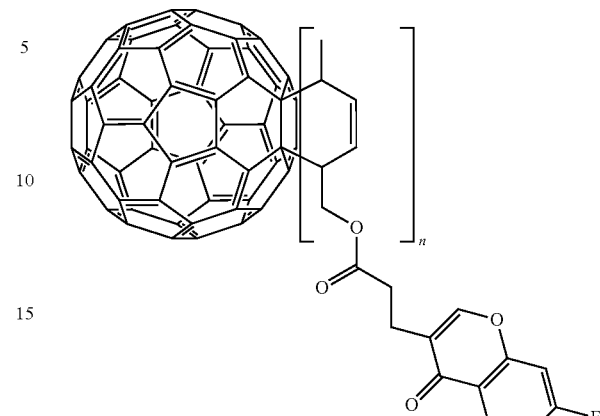
Chemical Formula 1-1-16
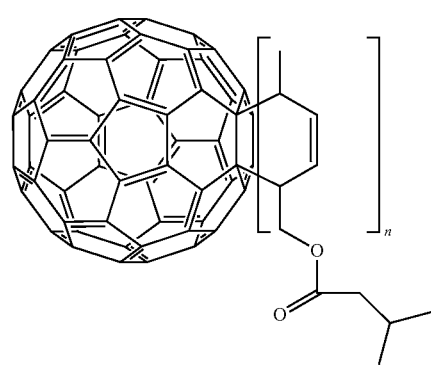
Chemical Formula 1-1-17
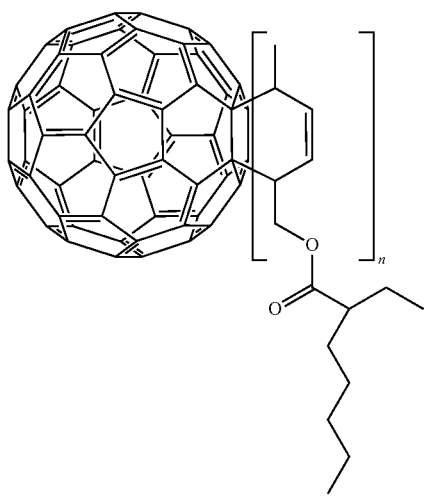

-continued
Chemical Formula 1-1-18
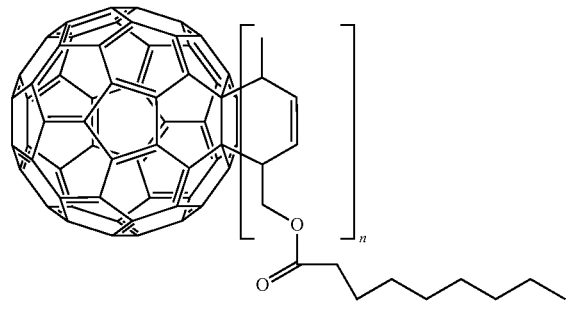
Chemical Formula 1-1-19
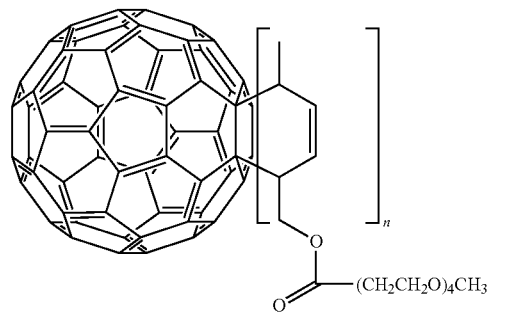
Chemical Formula 1-1-20
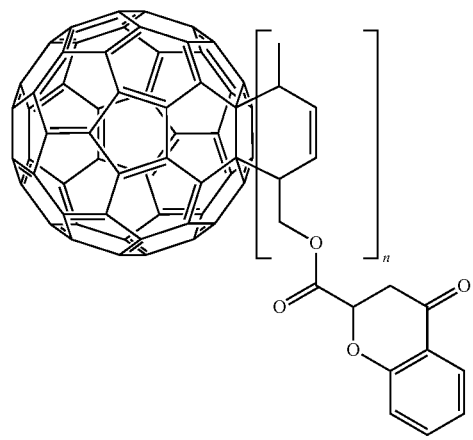
Chemical Formula 1-1-21
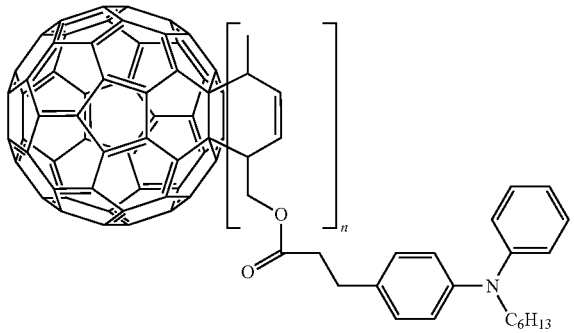
Chemical Formula 1-1-22
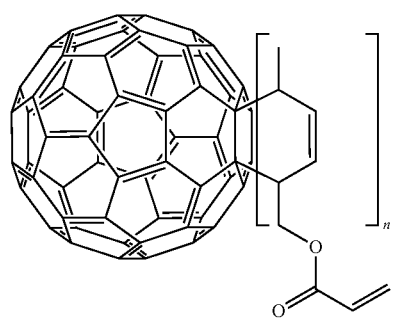
Chemical Formula 1-1-23
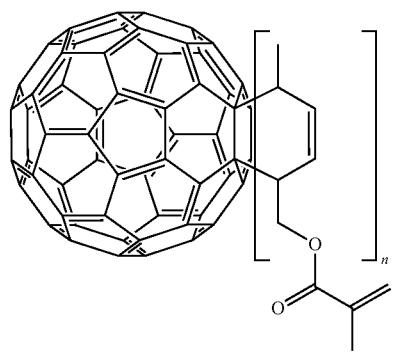
Chemical Formula 1-1-24
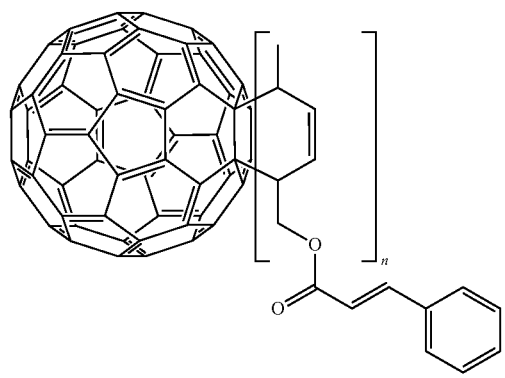
Chemical Formula 1-1-25
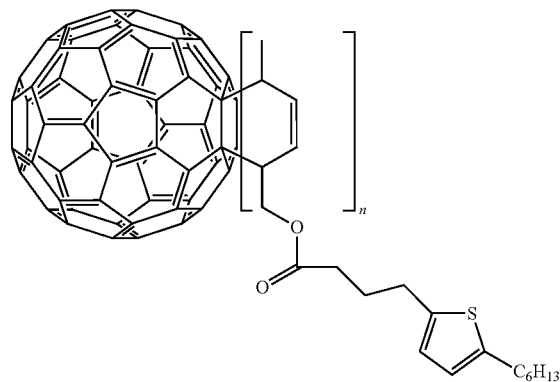

Chemical Formula 1-1-26

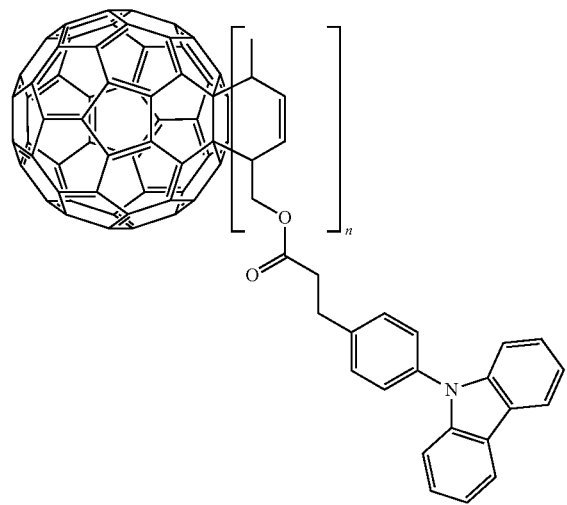

Chemical Formula 1-1-27

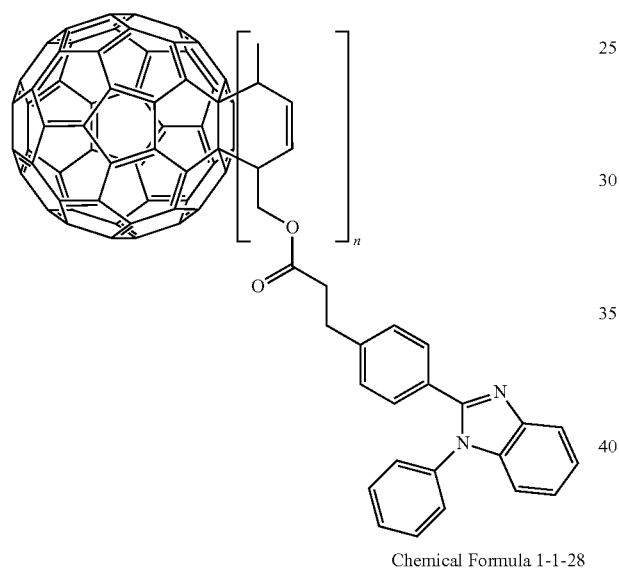

Chemical Formula 1-1-28

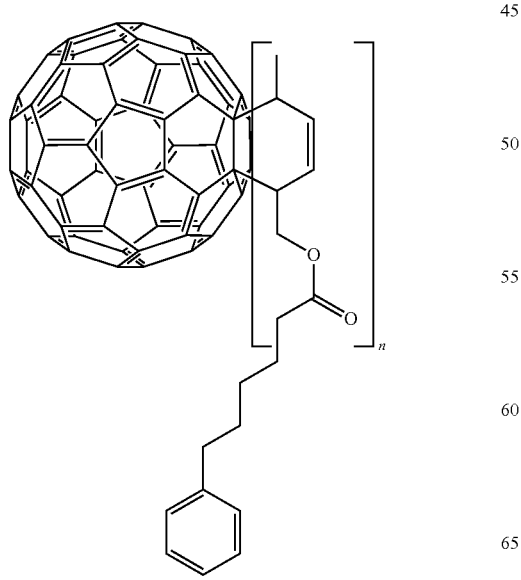

Chemical Formula 1-1-29

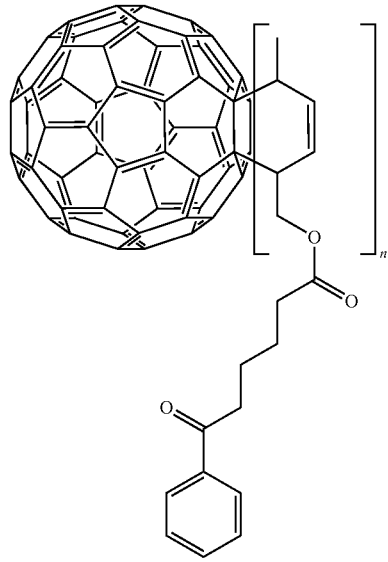

Chemical Formula 1-1-30

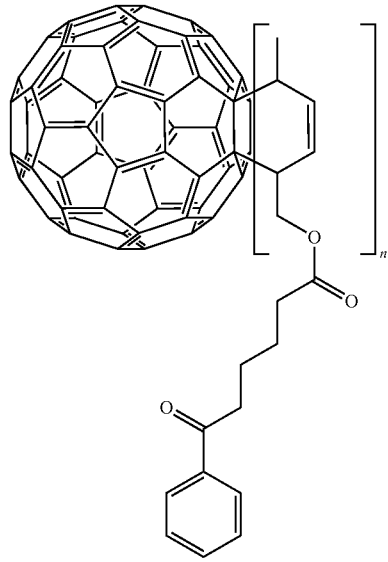

wherein n is the same as for Chemical Formula 1.

7. An organic electronic device comprising:
a first electrode;
a second electrode provided opposite to the first electrode; and
one or more organic material layers provided between the first electrode and the second electrode,
wherein the one or more organic material layers include the fullerene derivative of claim 1.

8. The organic electronic device of claim 7, which is selected from the group consisting of an organic light emitting device, an organic solar cell, and an organic transistor.

9. The organic electronic device of claim 7 is an organic solar cell.

10. The organic electronic device of claim 9, wherein the one or more organic material layers include a photoactive layer, the photoactive layer has a bilayer structure including an n-type organic material layer and a p-type organic material layer, and the n-type organic material layer includes the fullerene derivative.

11. The organic electronic device of claim 9, wherein the one or more organic material layers include a photoactive layer, the photoactive layer includes an electron donor material and an electron acceptor material, and the electron acceptor material includes the fullerene derivative.

12. The organic electronic device of claim 11, wherein the electron donor material and the electron acceptor material form a bulk heterojunction (BHJ).

13. The organic electronic device of claim 7, wherein the one or more organic material layers include a photoactive layer, another organic material layer is provided between the photoactive layer and the first electrode or the second electrode, and the another organic material layer provided between the photoactive layer and the first electrode or the second electrode includes the fullerene derivative.

14. The organic electronic device of claim 13, wherein the fullerene derivative included in the another organic material layer provided between the photoactive layer and the first electrode or the second electrode is an electron transfer material.

15. The organic electronic device of claim 13, wherein the another organic material layer provided between the photoactive layer and the first electrode or the second electrode includes a fullerene derivative layer including the fullerene derivative and a metal oxide layer, and the fullerene derivative layer is provided between the metal oxide layer and the photoactive layer.

16. The organic electronic device of claim 13, wherein the fullerene derivative included in the another organic material layer provided between the photoactive layer and the first electrode or the second electrode is an electron injection material.

17. The organic electronic device of claim 9, wherein the one or more organic material layers include a photoactive layer, and another organic material layer is provided between the photoactive layer and the second electrode, and the another organic material layer provided between the photoactive layer and the second electrode includes the fullerene derivative, and the first electrode is an anode electrode and the second electrode is a cathode electrode.

18. A fullerene derivative of Chemical Formula 1:

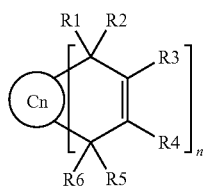

[Chemical Formula 1]

wherein:

n is an integer of 1 to 5;

when n is 2 or greater, structures within a parenthesis are the same as or different from each other;

Cn is fullerene of $C_{60}$ to $C_{120}$;

R1 to R6 are the same as or different from each other, and each is independently hydrogen, a halogen group, a nitro group, a cyano group, a carboxylic acid group, a hydroxyl group, a substituted or unsubstituted carbonyl group, a sulfo group ($-SO_3H$), a substituted or unsubstituted alkyl group, a substituted or unsubstituted alkoxy group, a substituted or unsubstituted cycloalkyl group, a substituted or unsubstituted alkenyl group, a substituted or unsubstituted ester group, a substituted or unsubstituted thioester group, a substituted or unsubstituted amide group, a substituted or unsubstituted ether group, a substituted or unsubstituted sulfonyl group ($-SO_2-$), a substituted or unsubstituted alkylthioxy group, a substituted or unsubstituted arylthioxy group, a substituted or unsubstituted alkylamine group, a substituted or unsubstituted arylamine group, a substituted or unsubstituted arylalkyl group, a substituted or unsubstituted heteroarylalkyl group, a substituted or unsubstituted aryl group, a substituted or unsubstituted heteroring group, or adjacent substituents bond to each other to form a substituted or unsubstituted hydrocarbon ring or a substituted or unsubstituted heteroring;

only one of R1 to R6 is

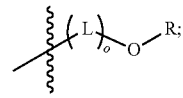

o is an integer of 1 to 3, and when o is an integer of 2 or greater, two or more Ls are the same as or different from each other;

L is an unsubstituted alkylene; and

R is a carboxylic acid group, a substituted or unsubstituted carbonyl group, an unsubstituted alkyl group, a substituted or unsubstituted cycloalkyl group, a substituted or unsubstituted alkenyl group, a substituted or unsubstituted ester group, a substituted or unsubstituted thioester group, a substituted or unsubstituted amide group, a substituted or unsubstituted sulfonyl group ($-SO_2-$), a substituted or unsubstituted arylalkyl group, a substituted or unsubstituted aryl group, or a substituted or unsubstituted heteroring group, when R is a substituted carbonyl group substituted with a substituted alkyl group, the substituted alkyl group of the substituted carbonyl group is substituted with one or more substituents selected from the group consisting of a halogen group, a nitro group, a cyano group, a hydroxyl group, a carbonyl group, a sulfo group, an allyl group, an alkoxy group, a cycloalkyl group, an alkenyl group, an ester group, an ether group, a sulfonyl group, a sulfoxy group, an arylalkyl group, an aryl group, and a heteroring group.

* * * * *